(12) United States Patent
Johs et al.

(10) Patent No.: US 7,535,566 B1
(45) Date of Patent: May 19, 2009

(54) BEAM CHROMATIC SHIFTING AND DIRECTING MEANS

(75) Inventors: Blaine D. Johs, Lincoln, NE (US);
Galen L. Pfeiffer, Lincoln, NE (US);
Jeffrey S. Hale, Lincoln, NE (US);
Christopher A. Goeden, Lincoln, NE (US); Brian D. Guenther, Lincoln, NE (US); Martin M. Liphardt, Lincoln, NE (US); Ping He, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 344 days.

(21) Appl. No.: 11/453,656

(22) Filed: Jun. 15, 2006

Related U.S. Application Data

(63) Continuation-in-part of application No. 10/613,051, filed on Jul. 7, 2003, now Pat. No. 7,099,006, and a continuation-in-part of application No. 09/945,962, filed on Sep. 4, 2001, now Pat. No. 7,075,649.

(60) Provisional application No. 60/229,755, filed on Sep. 5, 2000.

(51) Int. Cl.
*G01J 4/00* (2006.01)
*G02B 5/20* (2006.01)
*F21V 9/06* (2006.01)

(52) U.S. Cl. .............. 356/369; 356/364; 359/350; 359/359; 359/361

(58) Field of Classification Search ......... 356/364–369; 359/350, 358–361
See application file for complete search history.

(56) References Cited

U.S. PATENT DOCUMENTS

| | | | |
|---|---|---|---|
| 2,700,918 A | 2/1955 | Osterberg et al. | |
| 3,183,763 A | 5/1965 | Koester | |
| 3,992,104 A | 11/1976 | Watanabe | 356/117 |
| 4,053,232 A | 10/1977 | Dill et al. | 356/118 |
| 4,105,338 A | 8/1978 | Kuroha | 356/118 |
| 4,210,401 A | 7/1980 | Batten | 356/369 |
| 4,322,130 A * | 3/1982 | Ito et al. | 359/584 |
| 4,332,476 A | 6/1982 | Stenberg et al. | 356/369 |
| 4,355,903 A | 10/1982 | Sandercock | 356/632 |
| 4,373,817 A | 2/1983 | Coates | 356/384 |
| 4,556,292 A | 12/1985 | Mathyssek et al. | 350/394 |
| 4,647,207 A | 3/1987 | Björk et al. | 356/369 |
| 4,750,822 A | 6/1988 | Rosencwaig et al. | 356/445 |
| 4,826,321 A | 5/1989 | Coates et al. | 356/351 |
| 4,838,695 A | 6/1989 | Mansuripur et al. | 356/369 |
| 5,042,951 A | 8/1991 | Gold et al. | 356/369 |
| 5,045,704 A | 9/1991 | Coates | 250/372 |
| 5,329,357 A | 7/1994 | Bernoux et al. | 356/369 |
| 5,339,198 A * | 8/1994 | Wheatly et al. | 359/359 |
| RE34,783 E | 11/1994 | Coates | 250/372 |
| 5,373,359 A | 12/1994 | Woollam et al. | 356/328 |

(Continued)

FOREIGN PATENT DOCUMENTS

SU          1518728          10/1989

*Primary Examiner*—L. G Lauchman
(74) *Attorney, Agent, or Firm*—James D. Welch

(57) ABSTRACT

An electromagnetic beam chromatic shifting and directing means for use in reflectively directing a spectroscopic beam of electromagnetic radiation while simultaneously de-emphasizing intensity in a first range of wavelengths, (eg. the Visible wavelengths), and simultaneously relatively emphasizing intensity in another wavelength range, (eg. UV wavelengths).

11 Claims, 20 Drawing Sheets

U.S. PATENT DOCUMENTS

| | | | |
|---|---|---|---|
| 5,438,446 A * | 8/1995 | Brandt | 359/196 |
| 5,475,525 A | 12/1995 | Tournois et al. | 359/245 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/369 |
| 5,596,406 A | 1/1997 | Rosencwaig et al. | 356/327 |
| 5,596,411 A | 1/1997 | Fanton et al. | 356/369 |
| 5,608,526 A | 3/1997 | Piwonka-Corle et al. | 356/369 |
| 5,666,201 A | 9/1997 | Johs et al. | 356/369 |
| 5,706,212 A | 1/1998 | Thompson et al. | 356/525 |
| 5,757,494 A | 5/1998 | Green et al. | 356/369 |
| 5,872,630 A | 2/1999 | Johs et al. | 356/369 |
| 5,923,464 A * | 7/1999 | Braun | 359/350 |
| 5,946,098 A | 8/1999 | Johs et al. | 356/364 |
| 5,956,145 A | 9/1999 | Green et al. | 356/364 |
| 5,963,325 A | 10/1999 | Johs et al. | 356/364 |
| 5,963,327 A | 10/1999 | He et al. | 356/369 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,141,102 A | 10/2000 | Johs et al. | 356/364 |
| 6,268,917 B1 | 7/2001 | Johs | 356/369 |
| 6,456,376 B1 | 9/2002 | Liphardt et al. | 356/369 |
| 6,671,088 B2 * | 12/2003 | Goldstein | 359/361 |
| 7,206,125 B2 * | 4/2007 | Wang | 359/361 |

* cited by examiner

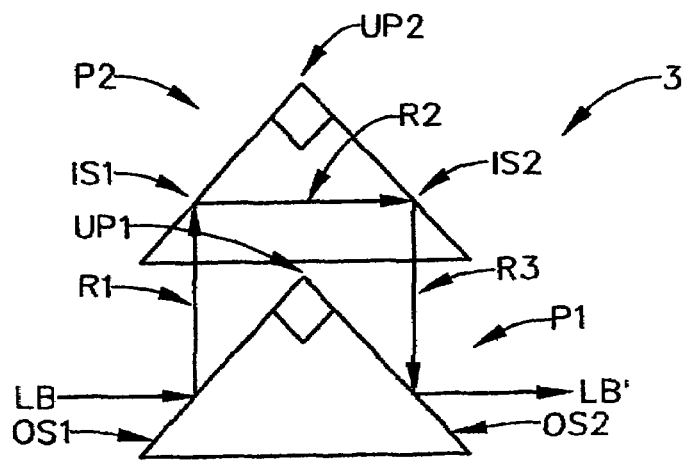
10f1
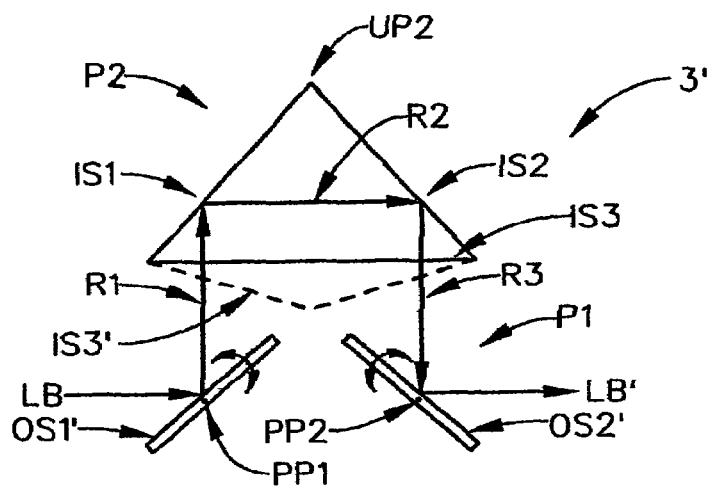
10f2
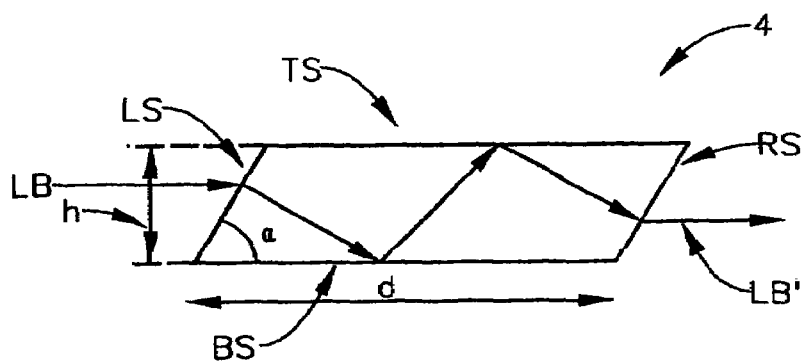
FIG. 10g

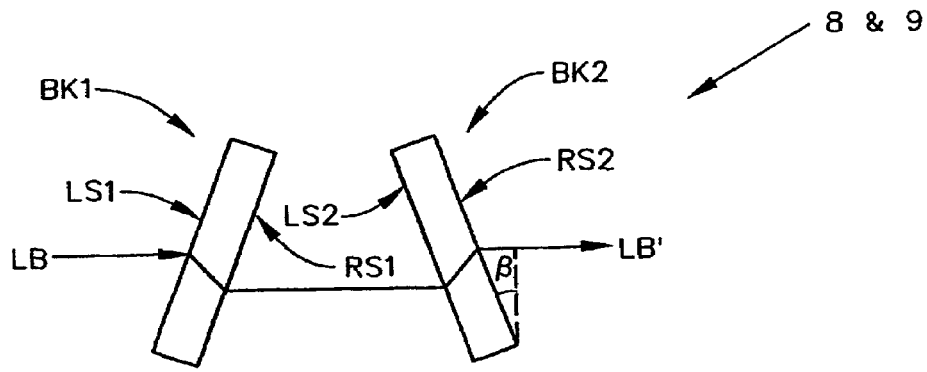
FIG10j1
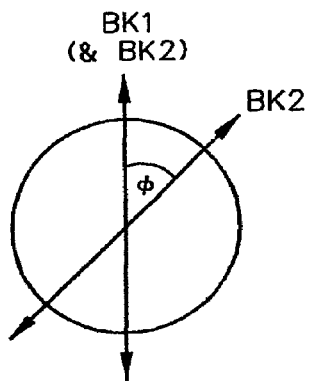
FIG. 10J2
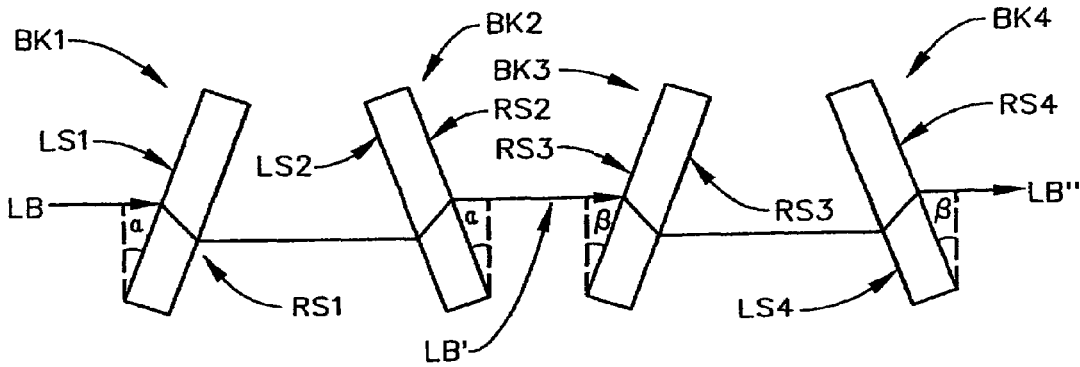
FIG. 10k1

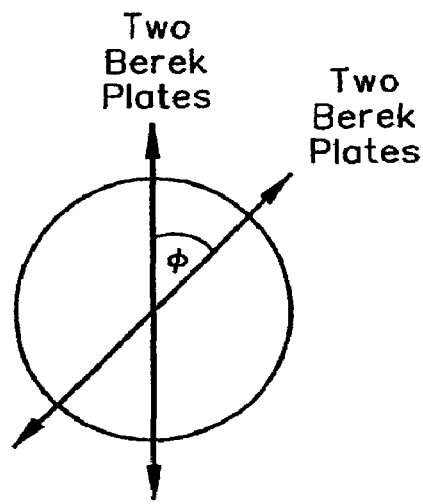
FIG. 10k2
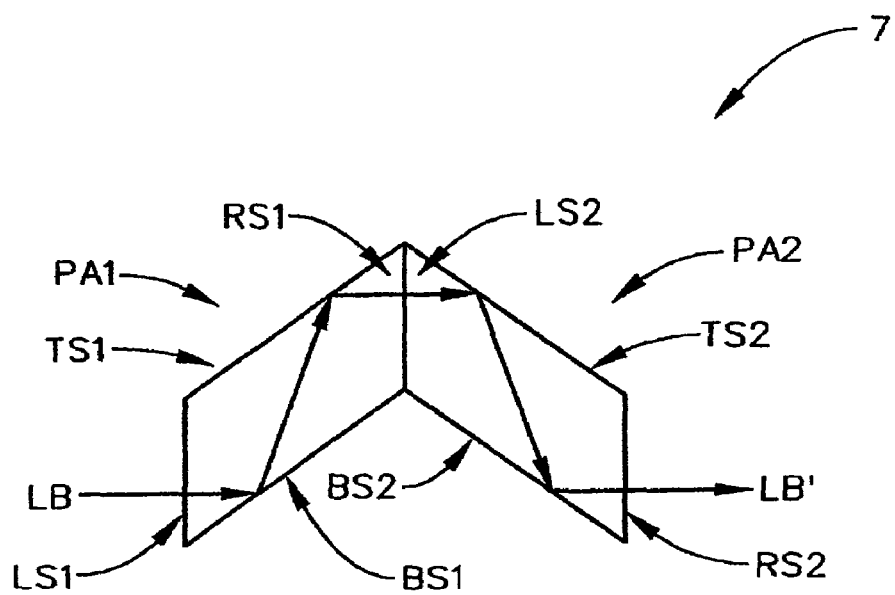
FIG. 10l

Providing a spectroscopic ellipsometer system comprising:
    a source of polychromatic electromagnetic radiation;
    a polarizer which remains fixed in position during data acquisition;
    a stage for supporting a sample system;
    an analyzer which remains fixed in position during data acquisition; and
    a detector system;
said spectroscopic ellipsometer system further comprising at least one means for discretely, sequentially, progressively modifying a polarization state of a beam of electromagnetic radiation provided by said source of polychromatic electromagnetic radiation through a plurality of polarization states, said means being present at at least one location selected from the group consisting of:
    between said polarizer and said stage for supporting a sample system; and
    between said stage for supporting a sample system and said analyzer.

For each of at least two ellipsometrically distinguished sample systems, obtaining at least one multi-dimensional data set(s) comprising magnitude as a function of wavelength and a function of a plurality of discrete settings of said at least one means for discretely, sequentially, progressively modifying a polarization state of a beam of electromagnetic radiation provided by said source of polychromatic electromagnetic radiation.

Providing a mathematical model of the ellipsometer system, including provision for accounting for the settings of said at least one means for discretely, sequentially, progressively modifying a polarization state of a beam of electromagnetic radiation provided by said source of polychromatic electromagnetic radiation.

By simultaneous mathematical regression onto said data sets, evaluating parameters in said mathematical model, including polarization state changing aspects of each of said plurality of discrete settings of said at least one means for discretely, sequentially, progressively modifying a polarization state of a beam of electromagnetic radiation provided by said source of polychromatic electromagnetic radiation.

FIG. 11

BEAM CHROMATIC SHIFTING AND DIRECTING MEANS

This Application is a CIP of Allowed application Ser. No. 10/613,051 Filed Jul. 7, 2003 now U.S. Pat. No. 7,099,006; and therevia Claims benefit of Provisional Application Ser. No. 60/229,755 filed Sep. 5, 2000. This Application is also a Continuation-in-Part of application Ser. No. 09/945,962 Filed Sep. 4, 2001 now U.S. Pat. No. 7,075,649, and therevia of Applications: Ser. No. 09/517,125 Filed Feb. 29, 2000; (now U.S. Pat. No. 6,084,674); and of Ser. No. 09/246,888 filed Feb. 8, 1999; (now U.S. Pat. No. 6,084,675); and further of Ser. No. 09/225,118 (now U.S. Pat. No. 6,084,674); Ser. No. 09/223,822 (now U.S. Pat. No. 6,118,537); Ser. No. 09/232,257 (now U.S. Pat. No. 6,141,102); Ser. No. 09/225,371 (now U.S. Pat. No. 6,100,981); Ser. No. 09/225,076 (now U.S. Pat. No. 5,963,325) which Applications depended from Ser. No. 08/997,311 filed Dec. 23, 1997, (now U.S. Pat. No. 5,946,098). Further, via the Ser. No. 09/246,888, this Application is a Continuation-In-Part of: Ser. No. 08/912,211 filed Aug. 15, 1997, (now U.S. Pat. No. 5,872,630), which Continued-In-Part from Ser. No. 08/530,892 filed Sep. 20, 1995, (now U.S. Pat. No. 5,666,201); and and is also a CIP of Ser. No. 08/618,820 filed Mar. 20, 1996, (now U.S. Pat. No. 5,706,212). In addition, priority is Claimed from: Ser. No. 09/162,217 filed Sep. 29, 1998 via above Applications.

TECHNICAL FIELD

The disclosed invention finds application in reflectometer, spectrophotometer, ellipsometer, polarimeter and the like systems, and more particularly is a reflective system for de-emphasizing the intensity of electromagnetic radiation intensity in one range of wavelengths, (eg. Visual wavelengths), and simultaneously relatively emphasizing intensity in other ranges, (eg. IR and/or UV wavelengths).

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

In general, modern practice of ellipsometry typically involves causing a spectroscopic beam of electromagnetic radiation, in a known state of polarization, to interact with a sample system at least one angle of incidence with respect to a normal to a surface thereof, in a plane of incidence. (Note, a plane of incidence contains both a normal to a surface of an investigated sample system and the locus of said beam of electromagnetic radiation and is measured in terms of a laboratory frame of reference). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system:

$$\rho = rp/rs = \mathrm{Tan}(\Psi)\exp(i\Delta)$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Spectroscopic Detector System.

Each of said components b.-i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. As described elsewhere in this Specification, another approach provides that no element be continuously rotated during data acquisition but rather that a sequence of discrete polarization states be imposed during data acquisition. This approach allows eliminating many costly components from conventional rotating element ellipsometer systems, and, hence, production of an "Ultra-Low-Complexity" ellipsometer system. It is noted, that nulling ellipsometers also exist in which elements therein are rotatable in use, rather than rotating. Generally, use of a nulling ellipsometer system involves imposing a linear polarization state on a beam of electromagnetic radiation with a polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

It is further noted that reflectometer systems are generally sequentially comprised of:

a. a Source of a beam electromagnetic radiation;
d. (optional additional element(s));
e. a sample system;
f. (optional additional element(s));
i. a Spectroscopic Detector System;

and that reflectometer systems monitor changes in intensity of a beam of electromagnetic radiation caused to interact with a sample system. That is, the ratio of, and phase angle between, orthogonal components in a polarized beam are not of direct concern.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Patents of which the Inventor is aware include those to Woollam et al, U.S. Pat. No. 5,373,359, Patent to Johs et al. U.S. Pat. No. 5,666,201 and Patent to Green et al., U.S. Pat. No. 5,521,706, and Patent to Johs et al., U.S. Pat. No. 5,504,582 are disclosed for general information as they pertain to ellipsometer systems.

Further Patents of which the Inventor is aware include U.S. Pat. Nos. 5,757,494 and 5,956,145 to Green et al., in which are taught a method for extending the range of Rotating. Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said Patents describes the presence of a variable, transmissive, bi-refringent component which is added, and the application thereof during data acquisition to enable the identified capability.

A Patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

A Patent to He et al., U.S. Pat. No. 5,963,327 is disclosed as it describes an ellipsometer system which enables providing a polarized beam of electromagnetic radiation at an oblique angle-of-incidence to a sample system in a small spot area.

A Patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Dill et al., U.S. Pat. No. 4,953,232 is disclosed as it describes a rotating compensator ellipsometer system.

Patents co-owned with this Application, which Patents Claim various Compensator Designs recited in Claims herein, and which Patents are incorporated hereinto by reference are:

U.S. Pat. No. 5,946,098 to Johs et al.;
U.S. Pat. No. 5,963,325 to Johs et al.;
U.S. Pat. No. 6,084,674 to Johs et al.;
U.S. Pat. No. 6,084,675 to Herzinger et al.;
U.S. Pat. No. 6,100,981 to Johs et al.;
U.S. Pat. No. 6,118,537 to Johs et al.;
U.S. Pat. No. 6,141,102 to Johs et al.

Patents cited in examination of said Patents included U.S. Pat. No. 4,556,292 to Mathyssek et al. and U.S. Pat. No. 5,475,525 to Tournois et al.

A Patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon. This Patent also describes calibration utilizing two sample substrates, which have different depths of surface coating.

Other Patents which describe use of reflected electromagnetic radiation to investigate sample systems are U.S. Pat. Nos. RE 34,783, 4,373,817, and 5,045,704 to Coates; and 5,452,091 to Johnson.

A Patent to Biork et al., U.S. Pat. No. 4,647,207 is disclosed as it describes an ellipsometer system which has provision for sequentially positioning a plurality of reflective polarization state modifiers in a beam of electromagnetic radiation. While said 207 patent mentions investigating a sample system in a transmission mode, no mention or suggestion is found for utilizing a plurality of transmitting polarization state modifiers, emphasis added. U.S. Pat. Nos. 4,210,401; 4,332,476 and 4,355,903 are also identified as being cited in the 207 patent. It is noted that systems as disclosed in these Patents, (particularly in the 476 patent), which utilize reflection from an element to modify a polarization state can, that if such an element is an essential duplicate of an investigated sample and is rotated ninety degrees therefrom, then the effect of the polarization state modifying element on the electromagnetic beam effect is extinguished by the sample.

A Patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,595,406 are also identified as they describe systems which impinge electromagnetic beams onto sample systems at oblique angles of incidence. The 406 patent provides for use of multiple wavelengths and multiple angles of incidence. For similar reasons U.S. Pat. No. 5,042,951 to Gold et al. is also disclosed.

A Patent to Osterberg, U.S. Pat. No. 2,700,918 describes a microscope with variable means for increasing the visibility of optical images, partially comprised of discrete bi-refringent plates which can be positioned in the pathway between an eyepiece and an observed object. Other Patents identified in a Search which identified said 918 patent are U.S. Pat. No. 3,183,763 to Koester; U.S. Pat. No. 4,105,338 to Kuroha; U.S. Pat. No. 3,992,104 to Watanabe and a Russian Patent, No. SU 1518728. Said other Patents are not believed to be particularly relevant, however.

A U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this Patent is not controlling where electromagnetic radiation carrying fiber optics are present.

A Patent to Chen et al., U.S. Pat. No. 5,581,350, is disclosed as it describes a method for regression calibration of ellipsometers.

As present invention preferred practice is to utilize a spectroscopic source of electromagnetic radiation with a relatively flat spectrum over a large range of wavelengths U.S. Pat. No. 6,628,917 to Johs is disclosed. Patents relevant thereto include U.S. Pat. No. 5,179,462 to Kageyama et al. is identified as it provides a sequence of three electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 patent. Another U.S. Pat. No. 5,296,958 to Roddy et al., describes a similar system which utilizes Thompson Prisms to similarly combine electromagnetic beams for laser source. U.S. Pat. Nos. 4,982,206 and 5,113,279 to Kessler et al. and Hanamoto et al. respectively, describe similar electromagnetic electromagnetic beam combination systems in laser printer and laser beam scanning systems respectively. Another U.S. Pat. No. 3,947,688 to Massey, describes a method of generating tuneable coherent ultraviolet light, comprising use of an electromagnetic electromagnetic beam combining system. A Patent to Miller et al., U.S. Pat. No. 5,155,623, describes a system for combining information beams in which a mirror comprising alternating regions of transparent and reflecting regions is utilized to combine transmitted and reflected beams of electromagnetic radiation into a single output beam. A Patent to Wright, U.S. Pat. No. 5,002,371 is also mentioned as describing a beam splitter system which operates to separate "P" and "S" orthogonal components in a beam of polarized electromagnetic radiation.

In addition to the identified Patents, certain Scientific papers are also identified.

A paper by Johs, titled "Regression Calibration Method for Rotating Element Ellipsometers", Thin Solid Films, 234 (1993) is also disclosed as it describes a mathematical regression based approach to calibrating ellipsometer systems.

Another paper, by Gottesfeld et al., titled "Combined Ellipsometer and Reflectometer Measurements of Surface Processes on Nobel Metals Electrodes", Surface Sci., 56 (1976), is also identified.

A paper by Smith, titled "An Automated Scanning Ellipsometer", Surface Science, Vol. 56, No. 1. (1976), is also mentioned as it describes an ellipsometer system which does not require any moving, (eg. rotating), elements during data acquisition.

Four additional papers by Azzam and Azzam et al. are also identified and are titled:

"Multichannel Polarization State Detectors For Time-Resolved Ellipsometry", Thin Solid Film, 234 (1993); and "Spectrophotopolarimeter Based On Multiple Reflections In A Coated Dielectric Slab", Thin Solid Films 313 (1998); and "General Analysis And Optimization Of The Four-Detector Photopolarimeter", J. Opt. Soc. Am., A, Vol. 5, No. 5 (May 1988); and "Accurate Calibration Of Four-Detector Photopolarimeter With Imperfect Polarization Optical Elements", J. Opt. Soc. Am., Vol. 6, No. 10, (October 1989);

as they describe alternative approaches concerning the goal of the present invention.

Even in view of the prior art, need remains for economical means for, in particular, de-emphasising Visual wavelength intensity and simultaneously relatively emphasizing both IR and UV wavelength intensities in ellipsometer, polarimeter and the like systems.

Further, it is noted that the parent Application hereto, Ser. No. 10/613,051 Filed Jul. 7, 2003 claimed a spectroscopic ellipsometer system which:

presents with stationary polarizer and analyzer during data acquisition; and utilizes a plurality of transmissive step-wise rotatable compensator means to effect a plurality of sequential discrete, rather than continuously varying, polarization states during said data acquisition; and which allows optional integrated combination with a reflectometer system via the sharing of a source of spectroscopic electromagnetic radiation and/or a spectroscopic multi-element detector system therewith.

In addition a calibration procedure for a spectroscopic ellipsometer system which involves the gathering of spectroscopic data at a plurality of discrete polarization states for each of some number of sample systems was alos disclosed in said 051. application.

DISCLOSURE OF THE INVENTION

The disclosed invention comprises at least one electromagnetic radiation chromatic shifting beam directing means for intercepting a beam of electromagnetic radiation having a specific intensity vs. wavelength spectrum, and providing reflected electromagnetic radiation with an intensity vs. wavelength spectrum wherein intensity in certain, (IR and/or UV), wavelength intensities are relatively emphasized. While any reflective chromatic shifting means which provides the result can be utilized, a particularly relevant readily available example is a Silicon Substrate with between about 500 and 1200 Angstroms of $SiO_2$ on its surface, said Silicon Substrate being positioned to receive electromagnetic radiation from, for instance, a Quartz halogen Source, (which provides an output wavelength spectrum wherein intensity is emphasized in the visual wavelength range), at an oblique angle. In combination with source intensity adjustment said chromatic shifting reflective means provides a reflected wavelength spectrum with intensity of longer (ie. toward the IR), and shorter (ie. toward the UV), wavelengths increased, and with Visual wavelengths de-emphasized.

The reason the chromatic shifting electromagnetic beam reflective means provides utility is that gain in an amplifier in a spectrometer detector that receives electromagnetic radiation conditioned thereby can be set higher when the intensity of higher intensity, (eg. Visual), Wavelength portion of the electromagnetic spectrum entered thereto is reduced. This increased gain is achieved without saturating the amplifier output response. Thus the increased spectrometer detector gain across the entire wavelength range can be beneficially applied to provide greater sensitivity in, for instance, the IR and UV range, as well as in maintaining such in the Visual range.

A disclosed invention method of providing a spectroscopic beam of electromagnetic radiation with more intensity in, for instance, IR and UV wavelength ranges, relative to the visible wavelength range, than is provided by a source of spectroscopic electromagnetic radiation comprises the steps of:

a) providing a source of spectroscopic electromagnetic radiation and an electromagnetic radiation chromatic shifting beam directing means for use in reflectively directing a spectroscopic beam of electromagnetic radiation while de-emphasizing visual wavelength intensity and relatively emphasizing both IR and UV wavelength intensities;

b) causing said source of spectroscopic electromagnetic radiation to provide a beam thereof and directing it to impinge upon said electromagnetic radiation chromatic shifting beam directing means at an oblique angle such that a reflected beam of electromagnetic radiation is produced, said chromatically shifted reflected beam of electromagnetic radiation having decreased intensity in visual wavelengths and relative thereto, increased intensity in IR and UV wavelengths.

Said method can further comprise generally increasing the intensity of the beam provided by said source of spectroscopic electromagnetic radiation, and causing said reflected beam to enter a detector with the IR and UV wavelength intensities being greater than they could be were the Visible wavelength intensity not reduced from that provided by the source, the reason being that the detector would saturate upon receiving the high Visible intensity.

The disclosed invention includes application of said electromagnetic radiation chromatic shifting beam directing means in a spectroscopic ellipsometer or polarimeter and the like. To so demonstrate, a design for an ellipsometer system is disclosed as comprising:

a source of electromagnetic radiation;
    Input Means comprising:
        optical fiber;
        coupler;
        colimating lens;
        beam directing mirror or beam chromatic shifting and directing means;
        polarizer;
        first rotatable compensator;
        Sample Supporting Stage;
    Output Means comprising:
        second rotatable compensator;
        analyzer;
        beam directing mirror or beam chromatic shifting and directing means;
        focusing lens;
        spectrometer.

In operation the Source of electromagnetic radiation provides spectroscopic electromagnetic radiation to one end of said optical fiber, a second end thereof being secured in the coupler. A beam of electromagnetic energy exiting said coupler is collimated by colimating lens and directed toward a selected beam directing mirror or beam chromatic shifting and directing means, from which it reflects. Said reflected beam is caused to pass through polarizer and the first rotatable compensator before being caused to impinge upon a sample which is held in position by said sample supporting stage. Electromagnetic radiation which reflects from said sample is directed to pass through second rotatable compensator and said analyzer before being caused to reflect from a selected beam chromatic shifting and directing means or a beam directing mirror, said reflected electromagnetic radiation is then caused to pass through focusing lens and enter spectrometer which comprises a multi-element detector system.

(It is noted that at least one chromatic shifting and directing means is selected to be present either before, after, or before and after the sample supporting stage).

A preferred embodiment of the disclosed invention provides for discrete manual Angle-of-Incidence manual setting of 65, 70, 75 and 90 degrees via positioning of the Input and Output Means, without need for tilt adjusting the Sample Supporting Stage, which is capable of receiving substrates of up to 8.5 inches in diameter. Said Sample Supporting Stage can be provided capability to automatically adjust position in the vertical "Z" direction. The input/output units have "home-sensors" present to enable easy setting of polarizer and analyzer positions. Typical spectral range is 360 to 380 through 1000 nm and the preferred Spectrometer is available from Ocean Optics, (eg. Model USB2000). The overall size of a preferred design is conveniently about 19 inches wide, 10.5 inches tall and 15 inches deep. Mica or calcite waveplates can be used as retarders, as can compensators as described later in this Specification. And, it should be appreciated that the presence of two rotatable compensators makes it possible to determine all elements of a Mueller Matrix.

A disclosed invention method of investigating a sample comprises the steps of:

a) providing an ellipsometer system such as disclosed above, which comprises at least one chromatic shifting and directing means in the pathway of the beam;
    b) while causing said source of electromagnetic radiation to provide a beam of spectroscopic electromagnetic radiation and interact with said sample and enter said spectrometer, causing at least one element selected from the group consisting of:
        polarizer;
        analyzer;
        first rotatable compensator;
        second rotatable compensator;

to be sequentially stepped through a progression of discrete polarization state setting positions, and at a plurality thereof taking data while all elements are stationary, said electromagnetic beam being also caused to reflect from said at least one chromatic shifting and directing means at some point between the source of electromagnetic radiation and said spectrometer.

Preferred practice involves holding the polarizer and analyzer stationary while sequentially rotating the first rotatable compensator and/or second rotatable compensator through a sequence of discrete positions.

It is also noted that use of the chromatic shifting and directing means is not limited to application in ellipsometer or polarimeter and the like systems in which a polarizer, analyzer, first compensator, second compensator or functionally similar element is/are stepped through a sequence of discrete polarization states, but can also be applied in such systems in which such elements are caused to continuously rotate during use and remain within the scope and breadth of the disclosed invention.

Further insight to spectroscopic ellipsometers in which the disclosed invention at least one chromatic shifting and directing means can be beneficially applied, is gleened from description substantially similar to what was previously disclosed in Co-Pending application Ser. No. 09/945,962, from which this Application Continues-in-Part. Said 962 application disclosed a spectroscopic ellipsometer system basically comprising:

a source of polychromatic electromagnetic radiation;
    a polarizer which is fixed in position during data acquisition;
    a stage for supporting a sample system;
    an analyzer which is fixed in position during data acquisition; and
    a multi-element spectroscopic detector system.

In addition, said ellipsometer system further comprises at least one means for discretely, sequentially, modifying a polarization state of a beam of electromagnetic radiation through a plurality of polarization states. The at least one means for discretely, sequentially, modifying a polarization state of a beam of electromagnetic radiation through a plurality of polarization states, is positioned between said polarizer and said stage for supporting a sample system, and/or and between said stage for supporting a sample system and said analyzer, and so that said beam of electromagnetic radiation transmits through a polarization state modifier element thereof in use. Said invention at least one means for discretely, sequentially, modifying a polarization state of a beam of electromagnetic radiation through a plurality of polarization states comprises a compensator which is mounted to allow step-wise rotation about the locus of a beam of electromagnetic radiation caused to pass therethrough.

It is also noted that removal of polarization state imposing or monitoring elements such as polarizer, compensator and analyzer in the systems described above, results in a reflectometer or spectrophotometer system.

While essentially any Compensator can be utilized, a preferred embodiment of the present invention provides that at least one of said at least one compensator(s), which is mounted to allow step-wise rotation about the locus of a beam of electromagnetic radiation caused to pass therethrough, be selected from the group consisting of:

- a single element compensator;
- a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;
- a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);
- a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);
- a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

(where the identifiers are shown in FIGS. 10a-10l).

Additional compensator systems, previously disclosed in patent application Ser. No. 08/997,311, (now U.S. Pat. No. 5,946,098), and CIP's therefrom, which are specifically within the scope of the invention and can be included in the selection group are:

- a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of material which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;
- a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of material which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a material with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of material with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further-comprising a third side which is oriented essentially horizontally and which is continuous with, and present below said first and second sides; said retarder system being made of a material with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation.

It is to be appreciated that said Compensator(s) can be caused to continuously rotate during data acquisition or be stepped through a series of discrete rotated positions and held stationary while obtaining data. Further, while not required, the present invention benefits from Compensator(s) designed to provide relatively constant, achromatic Polarization State Modification effects over a Spectroscopic range of wavelengths.

Where the polarizer in the spectroscopic ellipsometer system remains essentially fixed in position during data acquisition, it is noted that it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between "S" polarization transmission and reflection components is less, as a function of wavelength and electromagnetic beam angle-of-incidence to said beam combining means, when compared to that of the "P" components. The "P" component is far more affected, particularly around a Brewster angle condition, hence, where an "S" component, with reference to a beam combining system, is utilized, it is to be appreciated that variation in intensity of transmitted and reflected beams of electromagnetic radiation output from the beam combining system, as functions of wavelength and the angles of incidence of beams of electromagnetic radiation from sources of said transmitted and reflected beams of electromagnetic radiation, is minimized, as compared to variation which occurs in "P" components.

Before discussing the Method of Calibration of the discrete polarization state spectroscopic ellipsometer system, it is noted that the polarizer and analyzer thereof, which are essentially fixed in position during data acquisition, are not necessarily absolutely fixed in position between data acquisition procedures. Said polarizer and analyzer are preferably what is properly termed "Rotatable". That is they can be rotated to various positions by a user between data acquisitions, but they are not caused to be Rotating while data is being acquired. (Typical positioning of analyzer and polarizer azimuthal angles are plus or minus forty-five (+/−45) degrees).

Continuing, a method of calibrating a spectroscopic ellipsometer system comprises the steps of:

a. providing a spectroscopic ellipsometer system as described above herein;

said method further comprising, in any functional order, the steps of:

b. for each of at least two ellipsometrically different sample systems, obtaining at least one multi-dimensional data set(s) comprising intensity as a function of wavelength and a function of a plurality of discrete settings of said at least one means for discretely, sequentially, modifying a polarization state of a beam of electromagnetic radiation provided by said source of polychromatic electromagnetic radiation;

c. providing a mathematical model of the ellipsometer system, including provision for accounting for the settings of said at least one means for discretely, sequentially, modifying a polarization state of a beam of electromagnetic radiation provided by said source of polychromatic electromagnetic radiation utilized in step b; and d. by simultaneous mathematical regression onto said data sets, evaluating parameters in said mathematical model, including polarization state changing aspects of each of said plurality of discrete settings of said at least one means for discretely, sequentially, modifying a polarization state of a beam of electromagnetic radiation provided by said source of polychromatic electromagnetic radiation.

It is also mentioned that said method of calibrating a spectroscopic ellipsometer system can require, in the step b. obtaining of at least one multi-dimensional data set(s) comprising intensity as a function of wavelength and a function of a plurality of discrete settings of said at least one means for discretely, sequentially, modifying a polarization state of a beam of electromagnetic radiation, the obtaining of data from at least as many sample systems as are utilized discrete settings of said at least one means for discretely, sequentially, modifying a polarization state of a beam of electromagnetic radiation provided by said source of polychromatic electromagnetic radiation. However, if characteristics of a means for discretely, sequentially, modifying a polarization state of a beam of electromagnetic radiation are parameterized, say as a function of wavelength, are expressed by equations with a minimized number of parameters therein, it is possible to reduce the number of sample systems which must be utilized. That is, parameterization can be beneficially applied.

The preferred embodiment of the present invention involves positioning input and output polarizer/analyzer system azimuthal angles at typical fixed, nominal, constant plus or minus forty-five (+/−45) degrees, although use of polarizer and analyzer elements which are rotatable between data acquisition procedures is acceptable. It is noted that the static positioning of said input and output polarizer/analyzer system azimuthal angles greatly simplifies data acquisition, in that no phase sensors are required to detect rotational positioning are necessary, because synchronization is unnecessary. That is, as ellipsometric data is acquired asynchronously, the system requirements are greatly reduced as compared to ellipsometer systems which involve elements that are caused to rotate during data acquisition. Also, as alluded to, fiber optics are a preferred via for transporting electromagnetic radiation to and/or from the ellipsometer system.

It is again noted that a primary focus of the disclosed invention is the presence of an electromagnetic beam chromatic shifting and directing means for use in reflectively directing a spectroscopic beam of electromagnetic radiation while de-emphasizing intensity in visual wavelengths and while simultaneously relatively emphasizing both IR and UV wavelength intensities. While any functional element can be utilized, a preferred electromagnetic beam chromatic shifting and directing means comprises ailicon substrate with between 500 and 1500 Angstroms of silicon dioxide substantially uniformly present on a reflective surface thereof.

The present invention will be better understood by reference to the Detailed Description Section of this Specification, in combination with the Drawings.

SUMMARY

It is therefore a primary purpose and/or objective of the disclosed invention to teach a simple readily available chromatic shifting and directing means which de-emphasizes intensity at, for instance, visual wavelengths and relatively emphasizes intensity at, for instance, IR and UV wavelengths.

It is another primary purpose and/or objective of the disclosed invention to teach provision of at least one chromatic shifting and directing means in a reflectometer, spectrophotometer, ellipsometer or polarimeter or the like system, the purpose being to de-emphasize intensity at, for instance, visual wavelengths and relatively emphasize intensity at, for instance, IR and UV wavelengths, thereby allowing increased spectrometer/detector gain to be applied across the entire spectrum.

It is a specific purpose and/or objective of the disclosed invention to teach a system for and method of applying a Silicon Substrate with between about 500 and 1200 Angstroms of $SiO_2$ on its surface to accept electromagnetic radiation from a Source thereof, (which provides an output wavelength spectrum comprising relatively high intensity in the visual wavelength range), and provide electromagnetic radiation with a reflected wavelength spectrum having de-emphasized Visual wavelength intensity and relatively emphasizes longer (ie. toward the IR), and shorter (ie. toward the UV), wavelength intensities.

It is another purpose and/or objective of the disclosed invention to teach reflectometer, spectrophotometer, ellipsometer, polarimeter or the like systems in which a Silicon Substrate with between about 500 and 1200 Angstroms of $SiO_2$ on its surface accepts electromagnetic radiation from a Source thereof, (which provides an output wavelength spectrum wherein most the energy is in the visual wavelength range), and provides electromagnetic radiation with a reflected wavelength spectrum having intensity de-emphasized in Visual wavelengths and relatively emphasized in both longer (ie. toward the IR), and shorter (ie. toward the UV), wavelengths.

Other purposes and/or objectives will become clear from a reading of the Specification and Claims.

BRIEF DESCRIPTION OF THE DRAWINGS

FIGS. 10f1-10l show additional functional construction of compensator systems which are within the scope of the present invention.

FIG. 11 demonstrates the flow of a present invention method of calibration of the spectroscopic ellipsometer portion of the present invention.

DETAILED DESCRIPTION

Figure 1A:
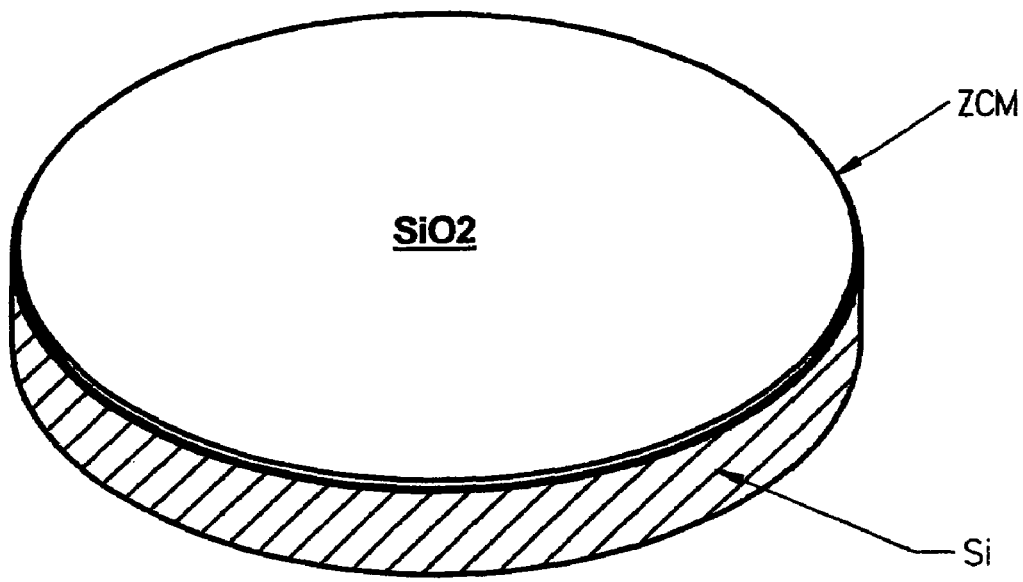
FIG. 1a shows a Beam Chromatic Shifting and Directing Means (ZCM) which comprises a Silicon Substrate (SI) upon the surface of which is present between about 500 and 1500 Angstroms, (nominal 600 or 1200 Angstroms), of Silicon Dioxide (SIO2).
Figure 1B:
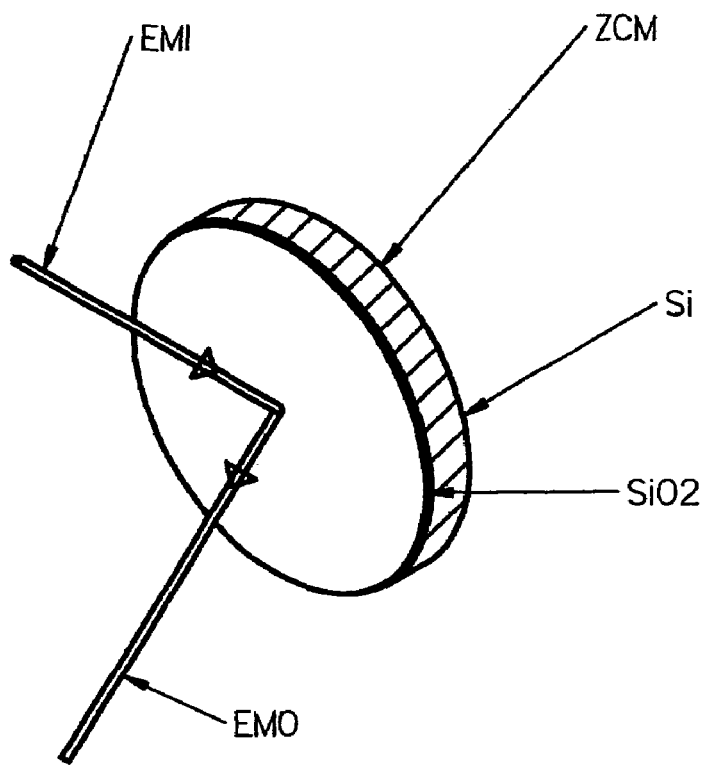
FIG. 1b indicates an incident Electromagnetic Beam (IEM) reflecting from beam chromatic shifting and directing means (ZCM) as beam (OEM).

Turning now to FIG. 1a, there is shown a Beam Chromatic Shifting and Directing Means (ZCM) which comprises a Silicon Substrate (SI) upon the surface of which is present between about 500 and 1500 Angstroms, (nominal 600 or 1200 Angstroms), of Silicon Dioxide (SIO2). FIG. 1b indicates an incident Electromagnetic Beam (IEM) reflecting from beam chromatic shifting and directing means (ZCM) as beam (EMO).

Figure 2:
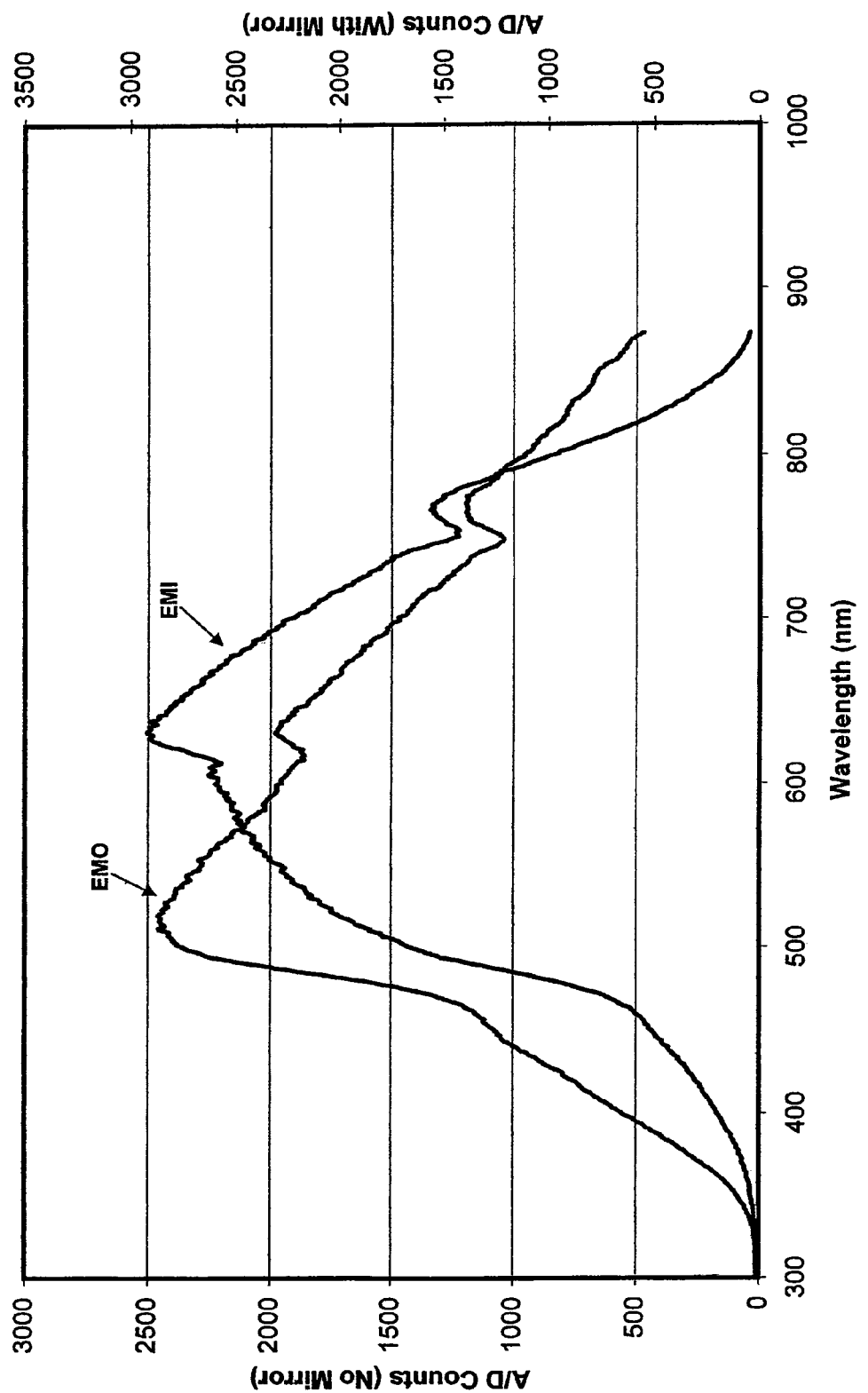
FIG. 2 demonstrates the effect of reflecting the Energy Spectrum provided by a Spectroscopic Source of Electromagnetic Radiation (ZQTH) off of a Beam Chromatic Shifting and Directing Means (ZCM).
Figure 4:
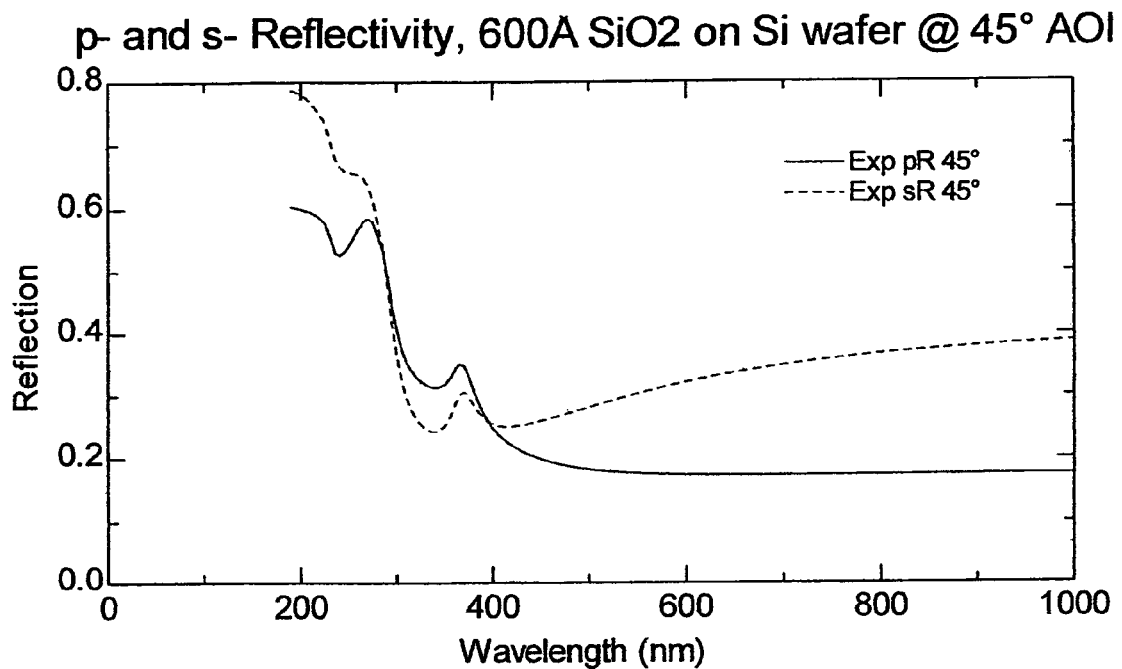
FIG. 4 is included to show results similar to those in FIG. 3, but where only 600 Angstroms of Silicon Dioxide are present on the surface of the Silicon instead of 1200 Angstroms.
Figure 3:
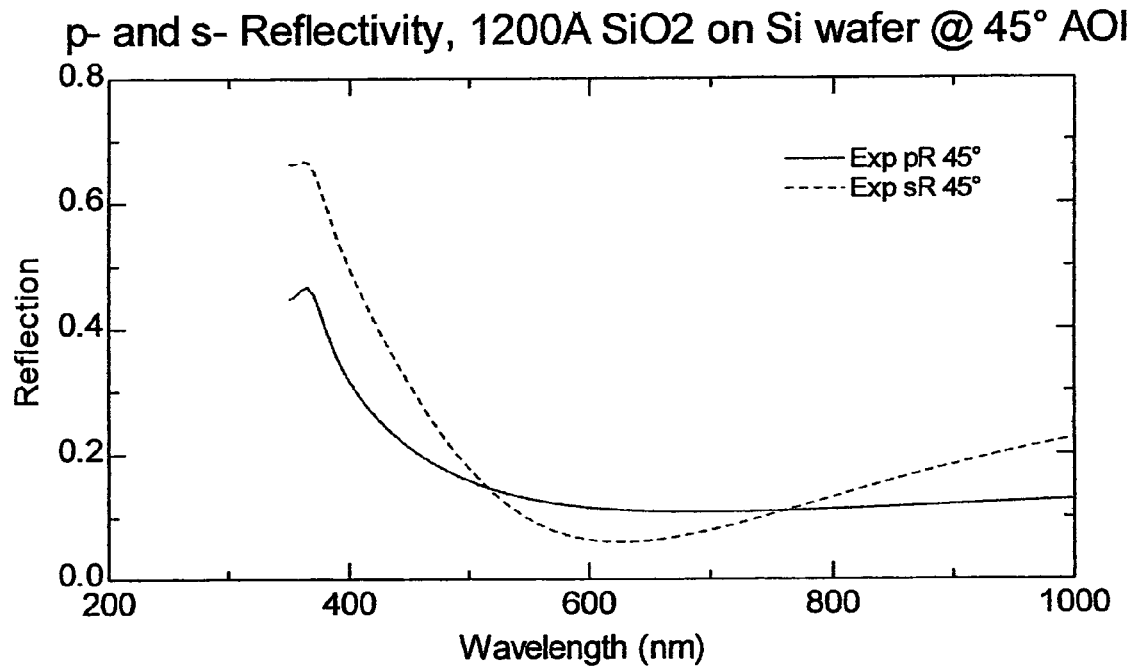
FIG. 3 shows the amount of "P" and "S" Polarization Component Energy, (each relative to a standard "1.0" as input), which reflects from such a Beam Chromatic Shifting and Directing Means (ZCM) as a function of wavelength.

FIG. 2 demonstrates the effect of reflecting the Energy Spectrum provided by a Spectroscopic Source of Electromagnetic Radiation (ZQTH), (see curve (EMI)) corresponding to Beam (EMI) in FIG. 1b, and the corresponding Shifted Energy Spectrum which results from reflection of said input Spectrum, (see curve labeled (EMO) corresponding to (EMO) in FIG. 1b)), from from a Silicon Substrate upon the surface of which is present Silicon Dioxide (see (ZCM) in FIG. 1b). FIG. 3 shows the amount of "P" and "S" Polarization Component Energy, (each relative to a standard "1.0" as input), which reflects from such a Beam Chromatic Shifting and Directing Means (ZCM) as a function of wavelength. FIG. 4 is included to show results similar to those in FIG. 3, but where only 600 Angstroms of Silicon Dioxide are present on the surface of the Silicon instead of 1200 Angstroms.

Figure 5:
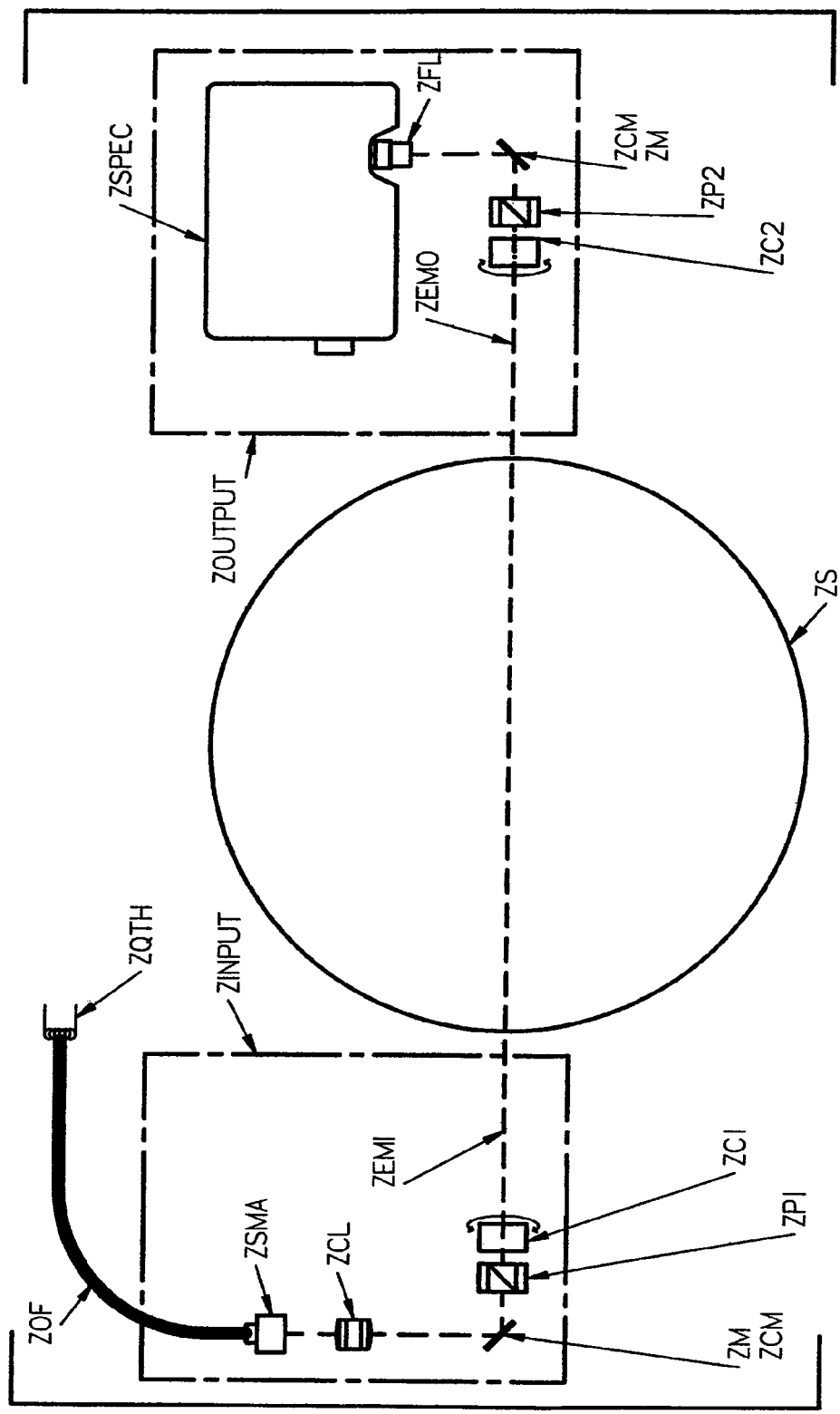
FIG. 5, an exemplary specific new design for an ellipsometer/polarimeter system utilizing a Beam Chromatic Shifting and Directing Means (ZCM).

Turning now to FIG. 5, an exemplary design for an ellipsometer/polarimeter system is presented as demonstrative of application of a Beam Chromatic Shifting and Directing Means (ZCM), and comprises:

Xenon or Quartz Halogen or the like Source (ZQTH);
Input means (ZINPUT) comprising:
  Optical Fiber (ZOF);
  Coupler (ZSMA);
  Colimating Lens (ZCL),
  beam directing mirror (ZM) or beam chromatic shifting and directing means (ZCM), but preferably beam directing mirror (ZM);
  Polarizer (ZP1);
  First Rotatable Compensator (ZC1);
  Sample Supporting Stage;
Output (ZOUTPUT) means comprising:
  Second Rotatable Compensator (ZC2);
  Analyzer (ZP2);
  beam directing mirror (ZM) or preferably beam chromatic shifting and directing means (ZCM);
  Focusing Lens (ZFL);
  Spectrometer (ZSPEC).

In operation the Xenon or Quartz Halogen or other Source (ZQTH) provides spectroscopic electromagnetic radiation to one end of said Optical Fiber (ZOF), a second end thereof being secured in Coupler (ZSMA). A beam of electromagnetic energy exiting said Coupler (ZSMA) is collimated by Colimating Lens (ZCL) and directed toward a Beam Directing Mirror (ZM), (or a beam chromatic shifting and directing means (ZCM)), from which it reflects. The reflected beam then passes through Polarizer (ZP1) and the First Rotatable Compensator (ZC1) before, as (ZEMI) being caused to impinge upon a Sample (ZS) which is held in position by a Sample Stage (see (ZSTG) in FIGS. 6-9). Electromagnetic radiation (ZEMO) effects from said Sample (ZS) is directed to pass through Second Rotatable Compensator (ZC2) and Analyzer (ZP2) before being caused to reflect from a Beam Chromatic Shifting and Directing Means (ZCM), (or a Beam Directing Mirror (ZM)). It is noted that the presence of a Beam Chromatic Shifting and Directing Means (ZCM) is a primary focus of novelty in the disclosed invention. The electromagnetic radiation reflected from said Beam Chromatic Shifting and Directing Means (ZCM) or a Beam Directing Mirror (ZM) is then caused to pass through Focusing Lens (ZFL) and enter Spectrometer (ZSPEC) which is a multi-element detector system. During data acquisition the Polarizer (ZP1) and/or Analyzer (ZP2) and/or Rotatable Compensator (ZC1) and/or Second Rotatable Compensator (ZC2) can be caused to continuously rotate, preferred operation provides that both the Polarizer (ZP1) or Analyzer (ZP2) be held stationary and that one or both of the First Rotatable Compensator (ZC1) and/or Second Rotatable Compensator (ZC2) be sequentially stepped through a progression of discrete polarization state setting positions. While data is collected, no component is moving. In particular this approach eliminates synchronization of rotating element and detector complexity.

Figure 6:
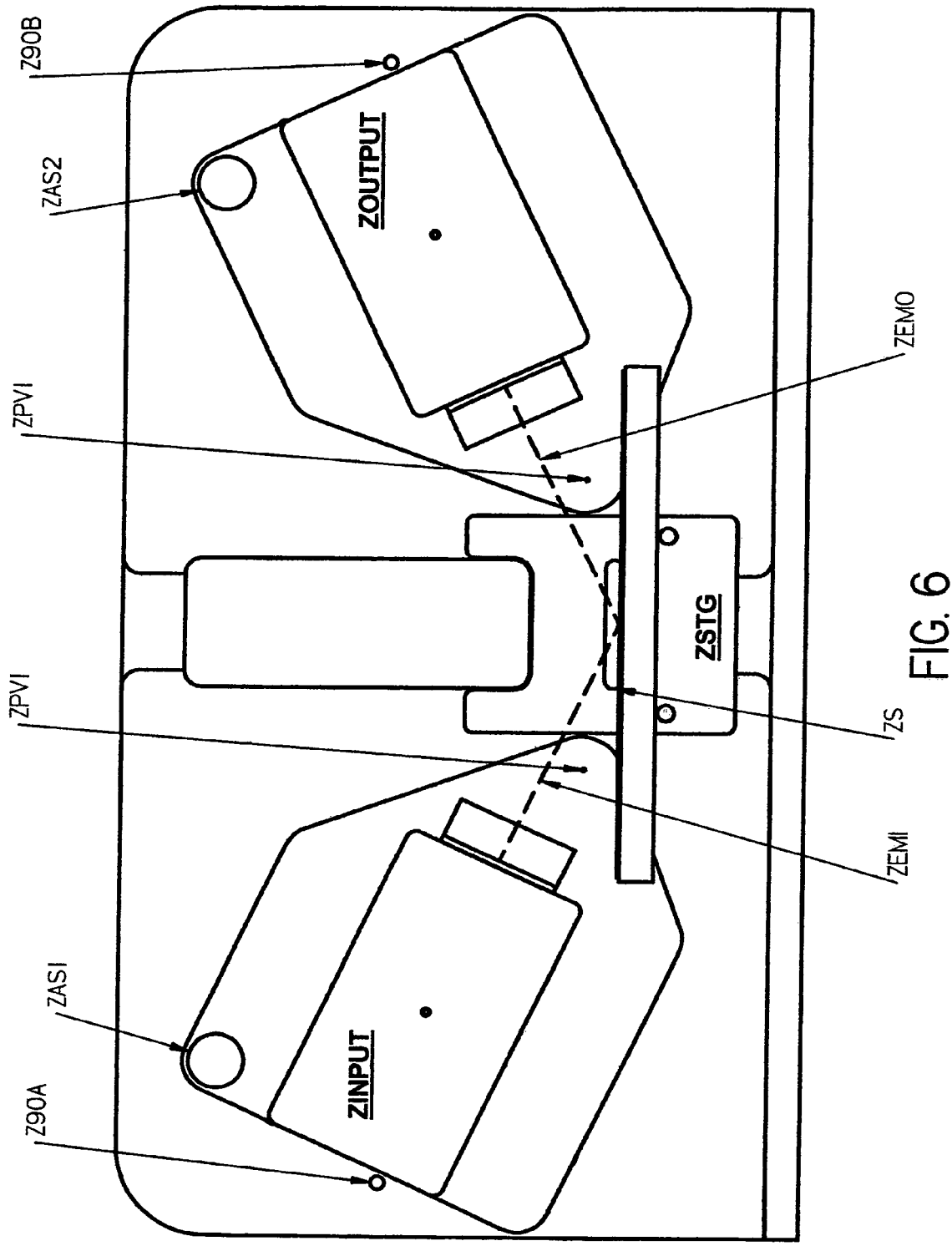
FIGS. 6-9 show front elevational views of the new design for an ellipsometer/polarimeter system of FIG. 5 in various states of Spectroscopic Electromagnetic Beam (ZEMI) to Sample (ZS) Angle-of-Incidence (AOI) adjustment.
Figure 7:
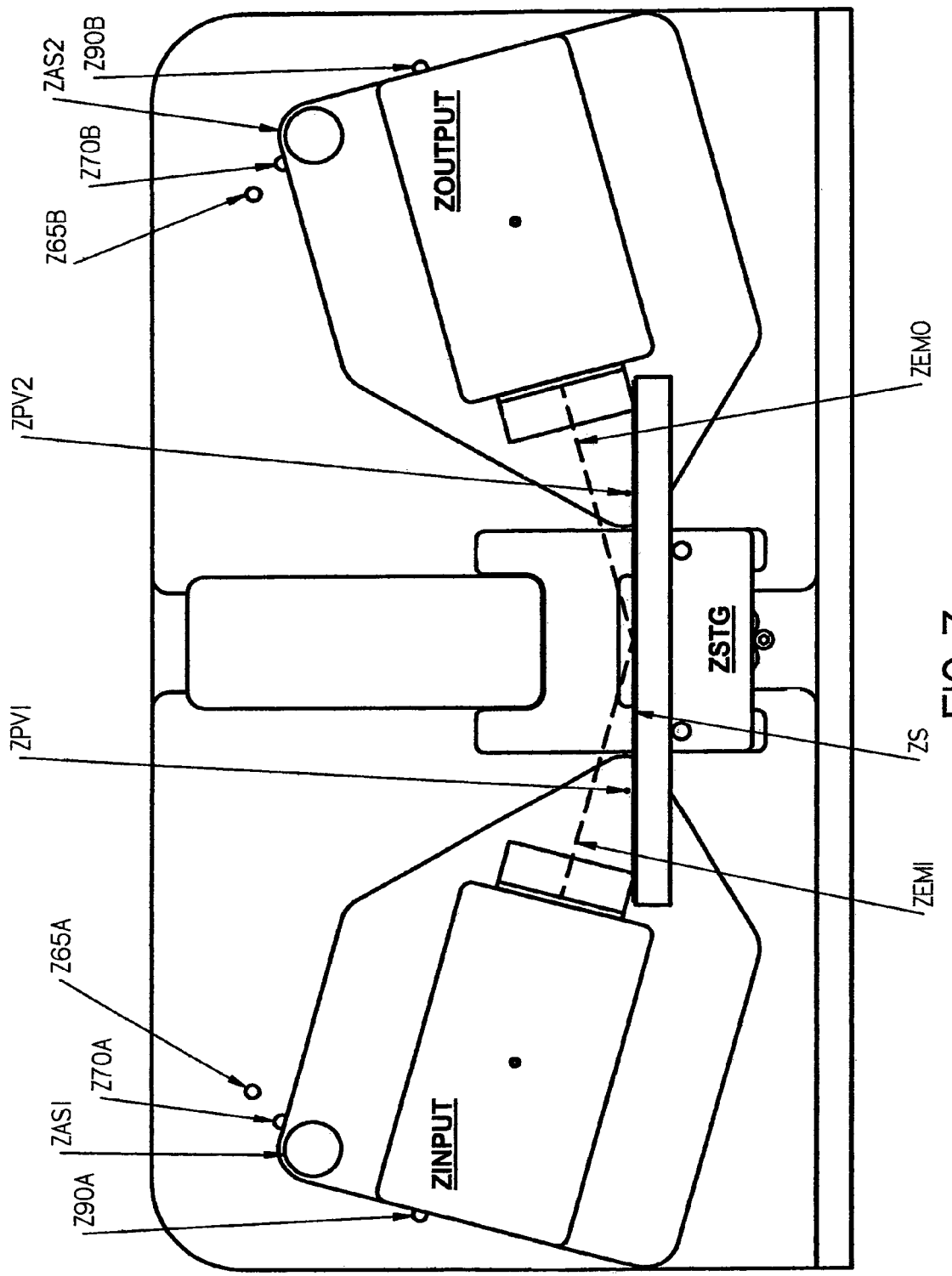
Figure 8:
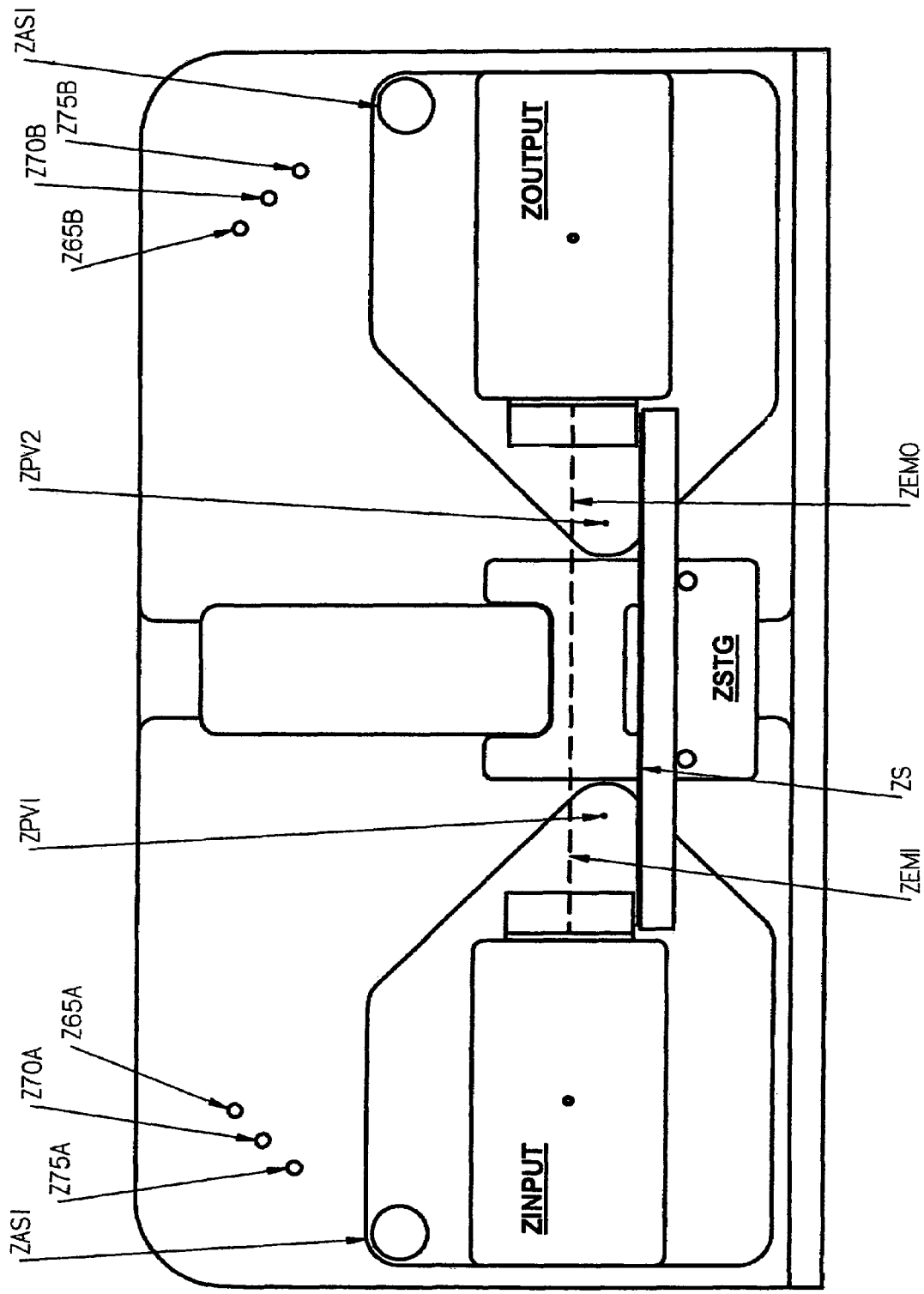
Figure 9:
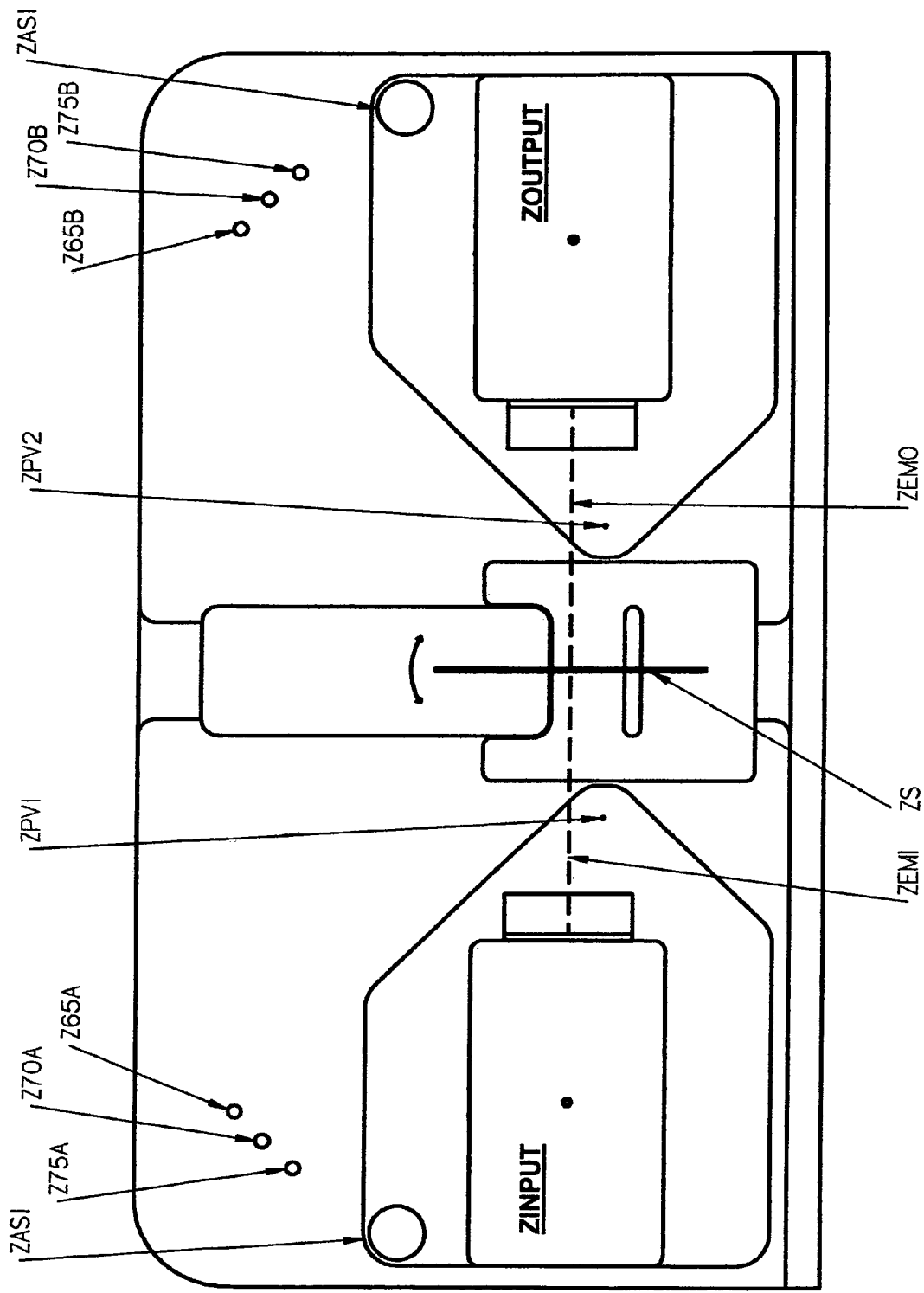

FIG. 6 shows a front elevational view indicating incident beam (ZEMI) exits the input means (ZINPUT), reflects off Sample (ZS), and as beam (ZEMO) enter Spectrometer (ZSPEC). Note that the Input Means (ZINPUT) and Output Means (ZOUTPU) each have Fixed Pivots (ZPVI) and Securing Pegs (ZASI) and (ZAS2) respectively. As better viewed in FIGS. 7-9, Securing Pegs (ZASI) and (ZAS2) allow easily securing Angles-Of-Incidence (AOI) of 65, 70, 75 and 90 degrees (straight-through or Normal by simply removal and re-insertion of the Securing Pegs (ZASI) and (ZAS2) in appropriate holes.

It is noted that the above example system for demonstrating an application of a Beam Chromatic Shifting and Directing Means (ZCM) is not to be considered a limiting application thereof. For instance, a Beam Chromatic Shifting and Directing Means (ZCM) could be applied in a Rotating Compensator Ellipsometer as taught in a Patent to Johs et al., U.S. Pat. No. 5,872,630, which is incorporated by reference hereinto. In addition, the Beam Chromatic Shifting and Directing Means (ZCM) could be applied in Rotating Polarizer or Rotating Analyzer or Modulation Element Ellipsometers.

Figure 14:
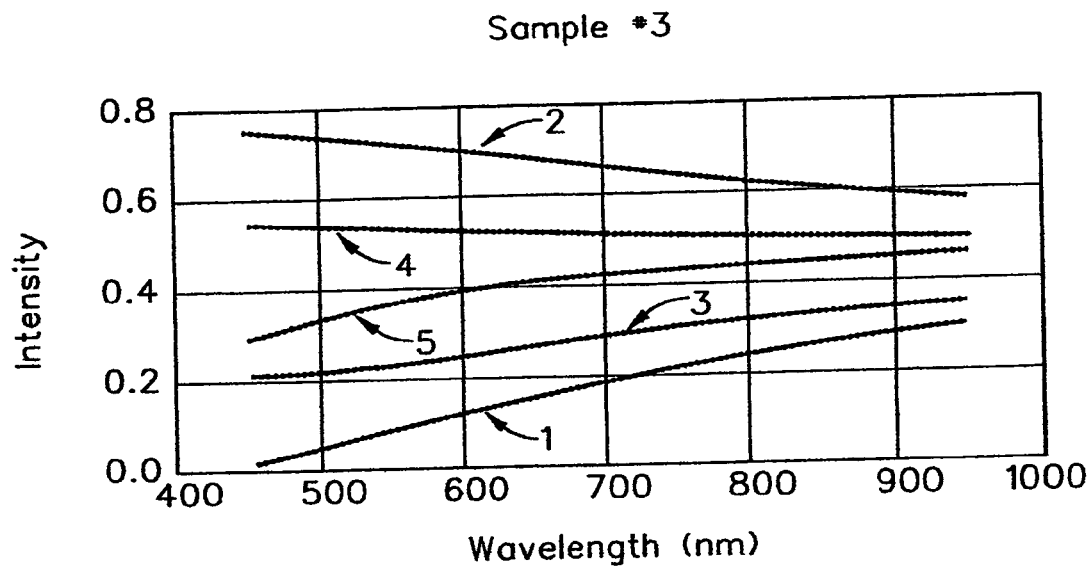
Figure 15:
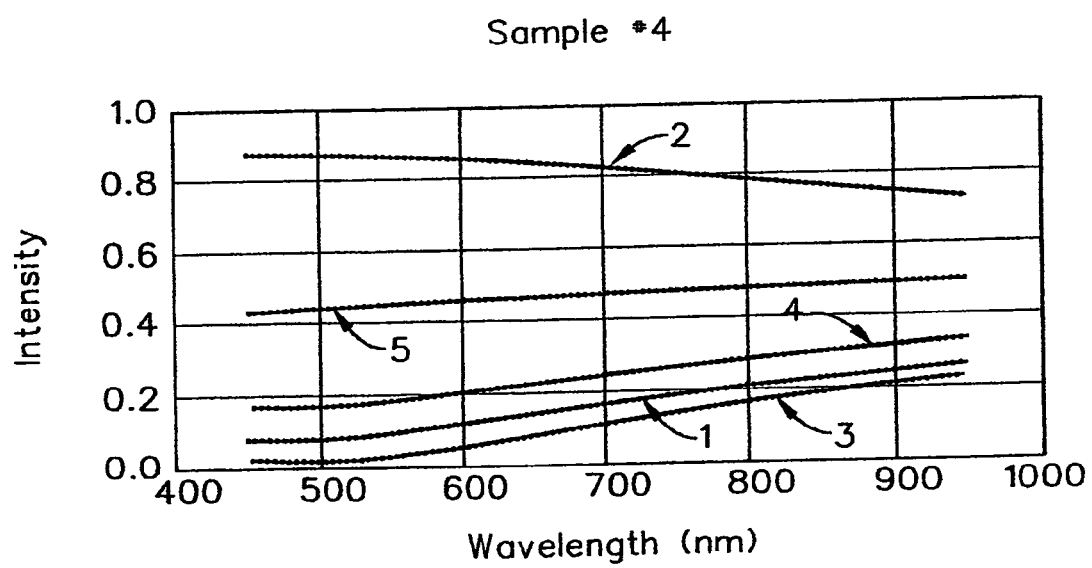
Figure 16:
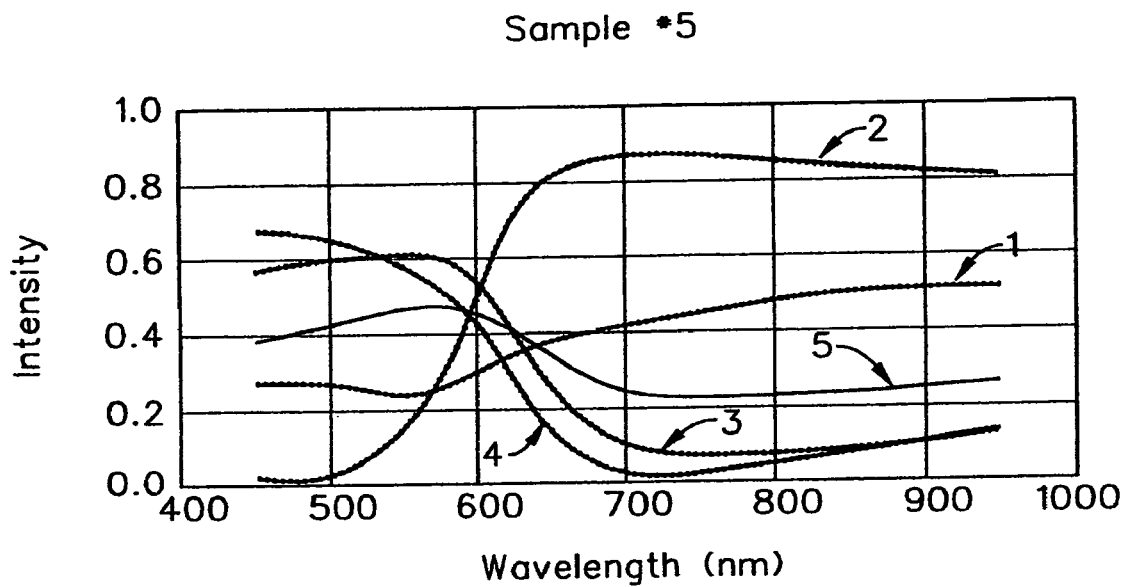
Figure 17:
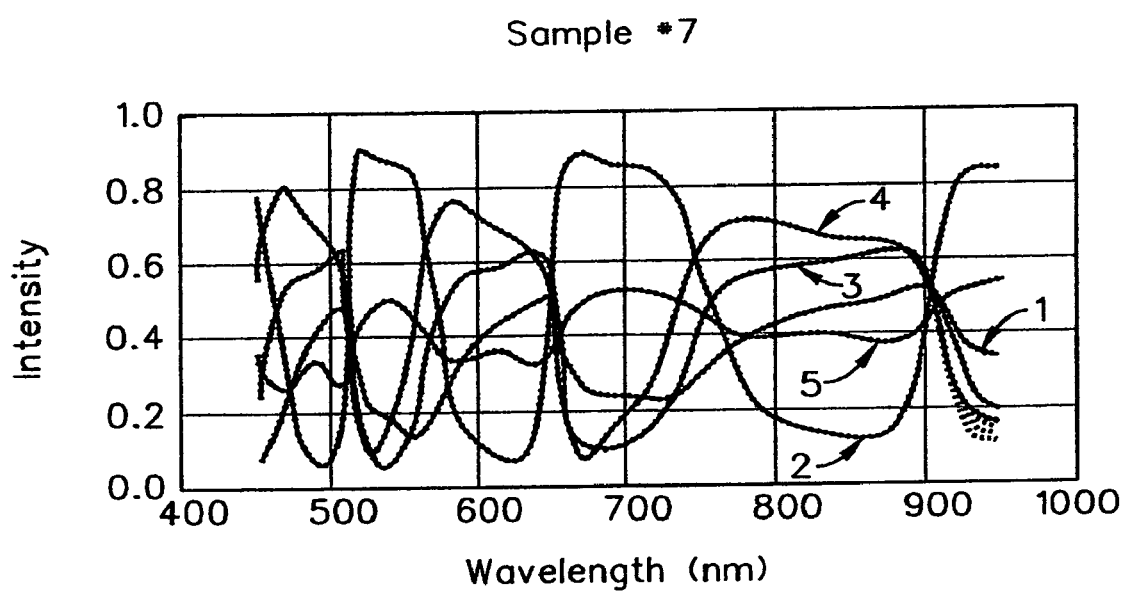
Figure 18:
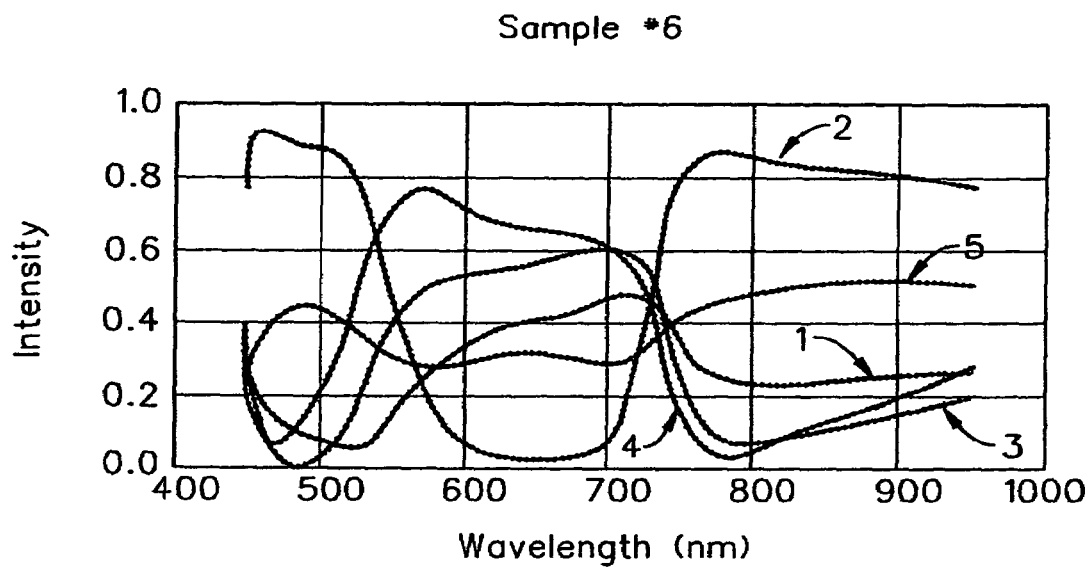

FIGS. 10e-10P demonstrate Compensators for application in the present invention, and FIGS. 14-16 show Retardation vs. Wavelength for Compensator designs which are Pseudo-Achromatic.

Figure 10A:
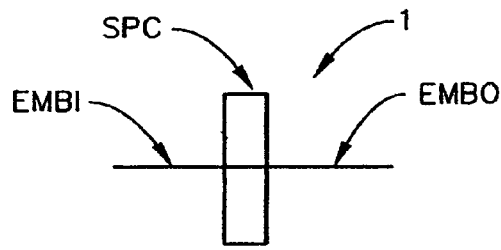
FIGS. 10a-10e demonstrate functional construction of preferred present invention compensator systems.
Figure 10B:
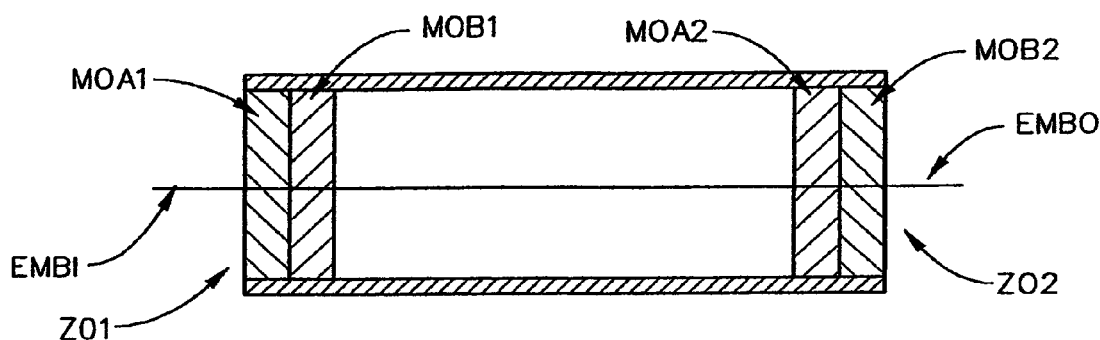

FIGS. 10a, 10b, 10c, 10d and 10e demonstrate that at least one Compensator can be applied as (DSP) or (DSP') in FIGS. 1 and 2, which at least one Compensator (DSP) and/or (DSP'), is, in use, rotated about the locus of the electromagnetic beam (EBI) or (EBO), by Compensator Rotation Stepping Means (CSM') and/or (CSM). That is, the presently disclosed invention then comprises a Discrete Polarization State Spectroscopic Ellipsometer System, with the clarification being that the Discrete Polarization State effecting means (DSP) and/or (DSP') is preferably a Rotatable Compensator, which during use is stepped through a plurality of discrete rotation angles, and then held motionless during data acquisition. While not limiting, a utility providing specific embodiment applies Psuedo-Achromatic Rotatable Compensators. (Note, FIGS. 14-16 show various Psuedo-Achromatic Retardation vs. Wavelength characteristics possible utilizing multiple element compensators, as shown in FIG. 10b).

Further, essentially any Compensator which can be placed into a beam of electromagnetic radiation can be applied, such as those disclosed in Claim 9 of U.S. Pat. No. 5,872,630, (which 630 patent is incorporated by reference hereinto):
  Berek-type;
  Non-Berek-type;
  Zero Order;
  Zero Order comprising a plurality of plates;
  Rhomb;
  Polymer;
  Achromatic Crystal; and
  Psuedo-Achromatic.

Figure 10C:
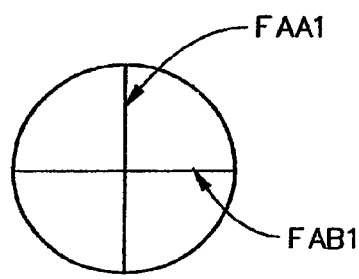
Figure 10D:
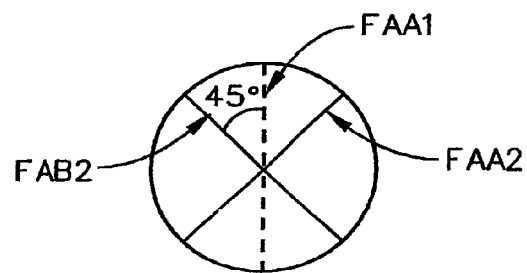
Figure 10E:
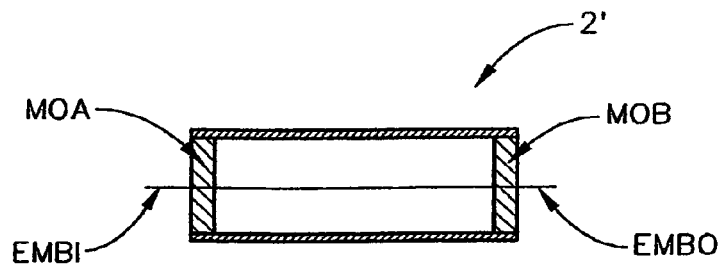

FIGS. 10a, 10b, 10c, 10d and 10e demonstrate functional construction of preferred present invention compensator systems. FIG. 10a simply exemplifies that a single plate (SPC) compensator (1) can be applied. FIG. 10b demonstrates construction of a compensator (2) from first (ZO1) and second (ZO2) effectively Zero-Order, (eg. Quartz or Bicrystalline Cadnium Sulfide or Bicrystalline Cadnium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 14b is a cross-sectional side view of a present invention preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength. FIGS. 10c and 10d are views looking into the left and right ends of the preferred present invention Compensator (PC) as shown in FIG. 10b, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (ZO1). (Note that the fast axis (FAA1) of the first effective Zero-Order Waveplate (ZO1) is shown as a dashed line in FIG. 10d, for reference). FIG. 10e demonstrates functional construction of another preferred compensator (2') which is constructed from two per se. single plate Zero-Order Waveplates (MOA) and (MOB), which are typically made of materials such as mica or polymer.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 10/1-10/ demonstrate additional compensators which can be applied in the present invention.

FIG. 10/1 shows that the first additional present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of material which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 10/1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (10) is present will require calibration to characterize the PSI-like component thereof.

FIG. 10/2 shows a variation (10') on FIG. 10/1, wherein the first triangular shaped element is replaced by two rotatable reflecting means, identified as (OS1') and (OS2'). This modification allows user adjustment so that the locus of an entering electromagnetic beam (LB') exits undeviated and undisplaced from an entering electromagnetic beam (LB).

FIG. 10g shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(∝)), where alpha (∝) is shown as an angle at which said right (RS) and left (LS) sides project from horizontal. Said retarder system (4) is made of a material with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha (∝) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

$$\frac{d}{h} = 2 \cdot \tan(\phi), \text{ where } \phi = \alpha + \sin^{-1}\left(\frac{\sin(90-\alpha)}{n}\right)$$

Figure 10H:
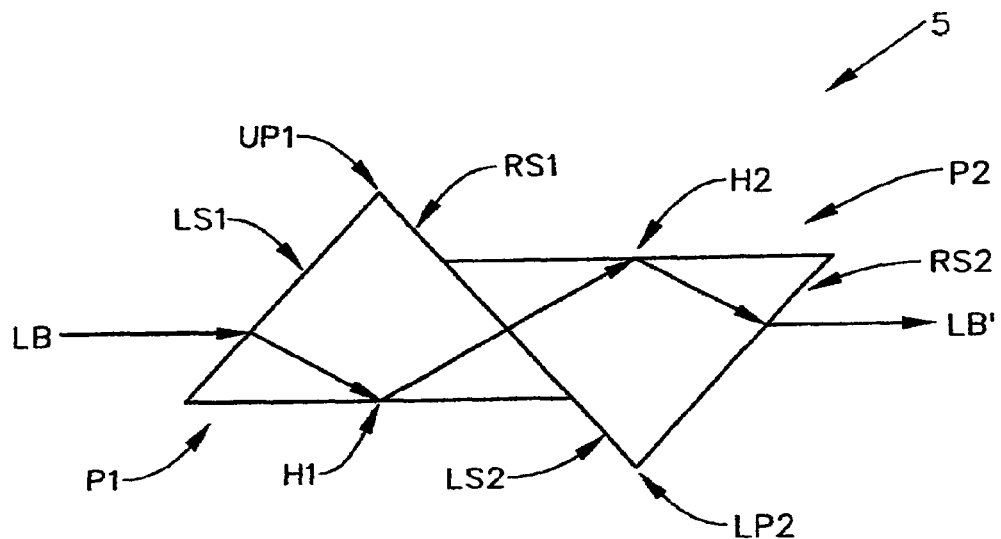

FIG. 10h shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of material with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various materials with various indicies of refraction, and coating(s) can be applied to one or both of the third sides (H1) and (H2) of said first (P1) and second (P2) triangular shaped elements to adjust retardation entered to an electromagnetic beam (LB1).

Figure 10I:
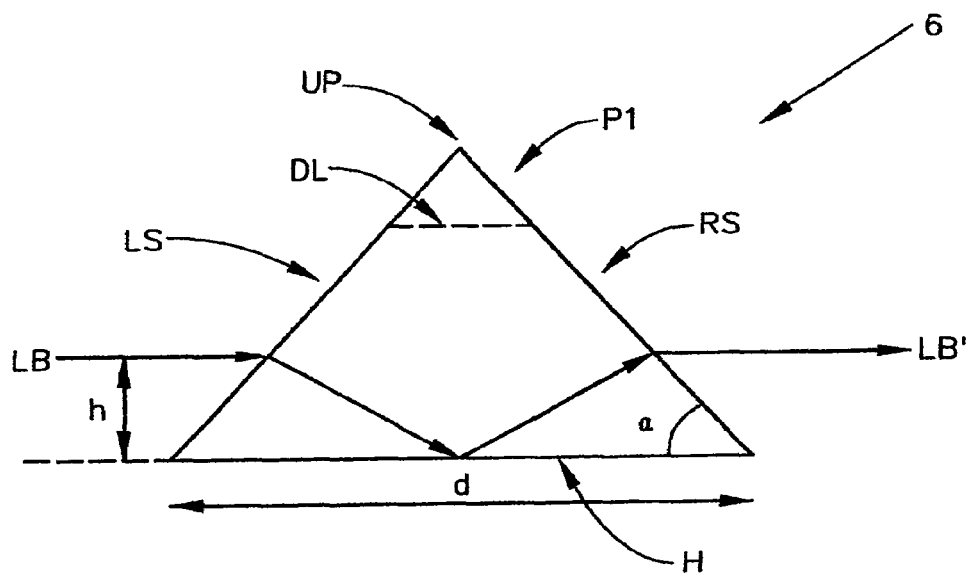
Figure 12:
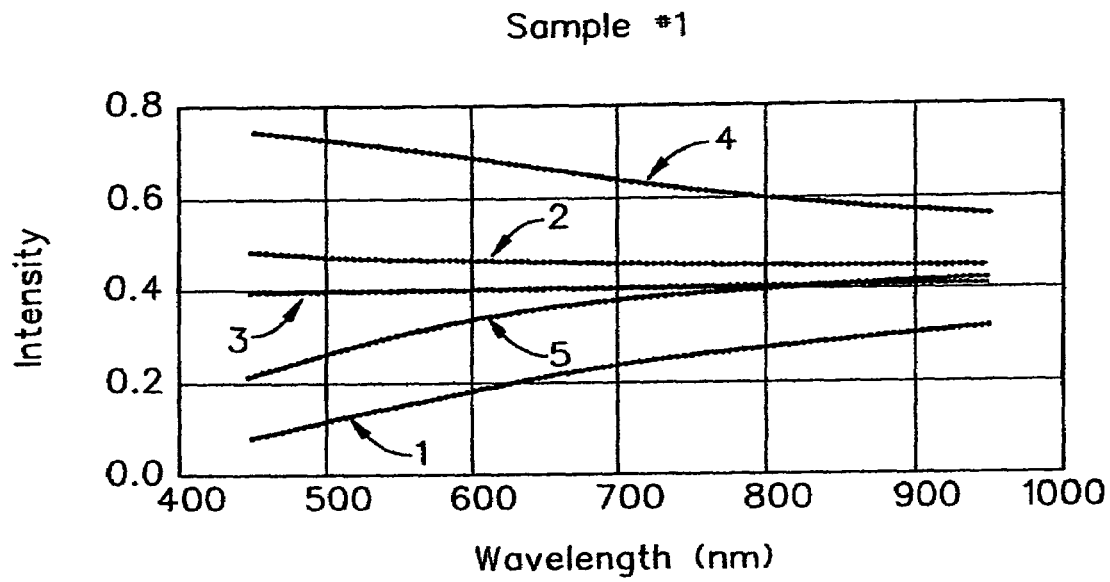
FIGS. 12-18 show Intensity vs. Wavelength for the seven (7) ellipsometrically different samples, obtained by fitting a mathematical model of the samples and the spectroscopic ellipsometer system by regression onto experimentally obtained data obtained at each of five (5) discrete polarization states.
Figure 13:
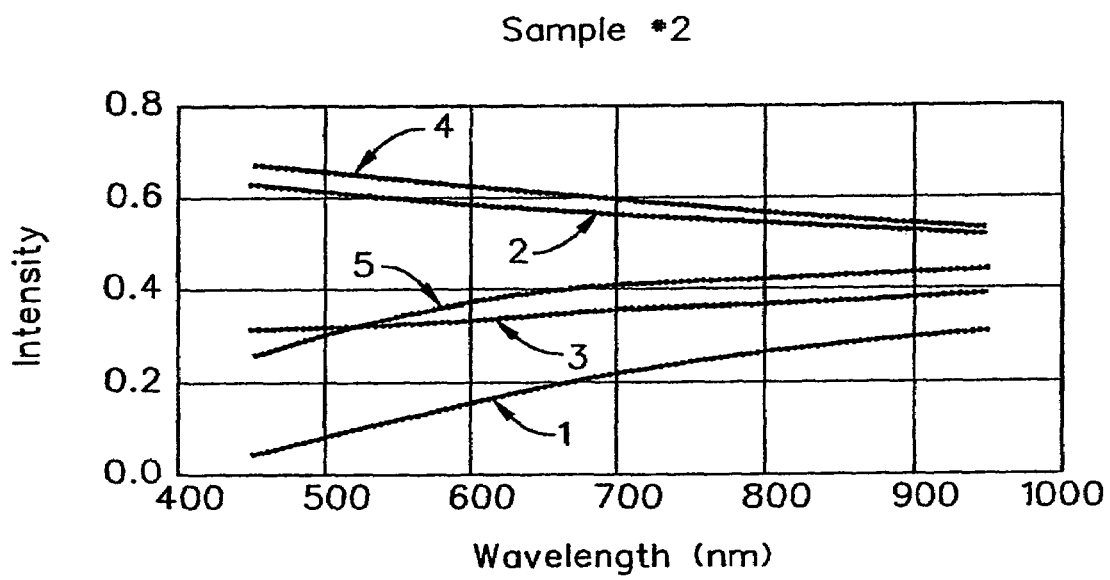

FIG. 10*i* shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a material with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 10*i* retarder system (6) is typically an isosceles prism which is available off-the-shelf with an angle alpha ($\alpha$) of forty-five (45) degrees. As long as the input electromagnetic beam (LB) height (h) is chosen in accordance with the formula:

$$d = 2h\left(\frac{1}{\tan(\alpha)} + \tan(\phi)\right), \text{ where } \phi = \alpha + \sin^{-1}\left(\frac{\sin(90-\alpha)}{n}\right)$$

in conjunction with the index of refraction (n) of the material from which the retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

FIG. 101 shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of material with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 10*j*1 shows that the sixth additional present invention retarder system (8) comprises first (BK1) and second (BK2) Berek-type retarders which each have an optical axes essentially perpendicular to a surface thereof. As shown by FIG. 10*j*2, each of said first (BK1) and second (BK2) Berek-type retarders can have fast axis which are oriented other than parallel to one another, but for the presently described retarder system it is assumed that the fast axes are aligned, (ie. an angle PHI ($\phi$) of zero (0.0) degrees exists between fast axes of the two Berek-type (BK1) and (BK2) plates in FIG. 10*j*1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately half of achieved retardence. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 10j2 offset angle PHI ( ) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 10k1 serves as the pictorial reference for the eighth additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 10k2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB") passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth additional present invention retarder system (11) is also pictorially represented by FIG. 10k1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different.

Further, as described in the Disclosure of the invention Section of this Specification, as the polarizer in the present invention spectroscopic ellipsometer system remains fixed in position during data acquisition, it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between transmission and reflection "S" polarization components is less, as a function of wavelength and electromagnetic beam angle-of-incidence to said beam combining means, compared to that between the "P" components.

It is also noted that a suitable electromagnetic beam combining (BCM) means can be made of glass or a fused silica plate, (preferably uncoated), and can also be "Hot Mirrors" which reflect IR and transmit visual wavelengths, or "Cold Mirrors" which reflect visible and transmit IR; mirror-type Beamsplitters or Pellicle Beamsplitters, such as described in Edmund Industrial Optics Catalog Number N997A.

It is also generally noted that the present invention spectroscopic ellipsometer system can, but not necessarily, utilize Zeiss Diode Array Spectrometer Systems identified by manufacturer numbers in the group: (MMS1 (1000-1150 nm); UV/VIS MMS (190-7100 nm); UV MMS (190-400 nm); and IR MMS (900-2400 nm)) as Detector System (DET). Said identified Zeiss systems provide a very compact system comprising a multiplicity of Detector Elements and provide focusing via a Focusing Element, Slit, and single concave holographic grating dispersive optics. However, any functional multi-element spectroscopic Detector arrangement is within the scope of the present invention.

For insight, FIG. 11 demonstrates the flow of a method of calibration of the spectroscopic ellipsometer described above.

FIGS. 12-18 show Intensity vs. Wavelength for the seven (7) ellipsometrically different samples at each of five (5) imposed polarization states. Results shown in FIGS. 5-7 respectively, are for Samples identified as 1, 2, 3, 4, 5, 6, and 7, which respectively have Oxide depths atop thereof of, (in Angstroms), 17.50; 103.0; 193.0; 508.0; 1318.0; 4817.0 and 9961.0.

Figure 19:
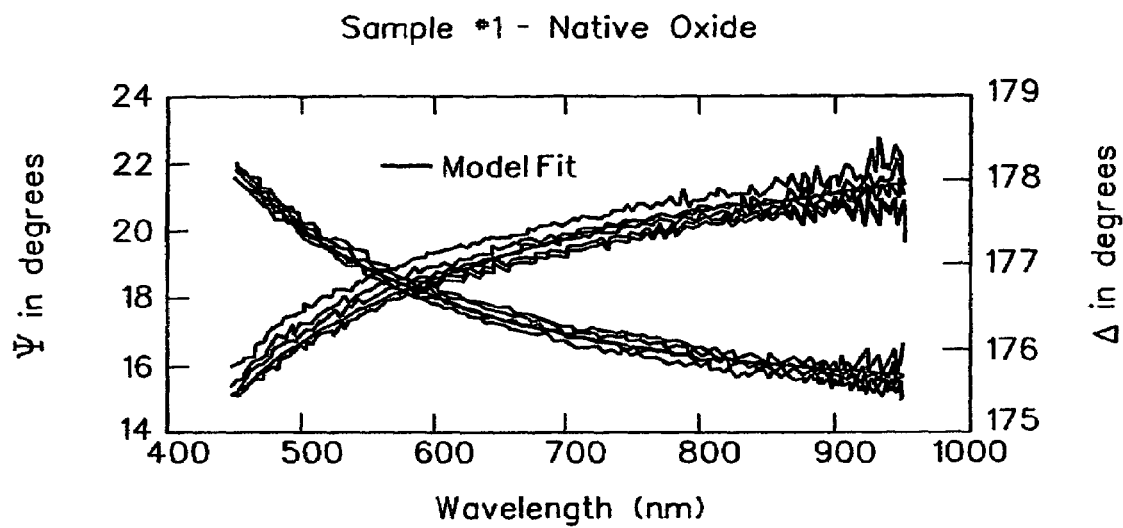
FIGS. 19 & 20 show PSI and DELTA values obtained for samples with thin and thick layers of Oxide thereupon.
Figure 20:
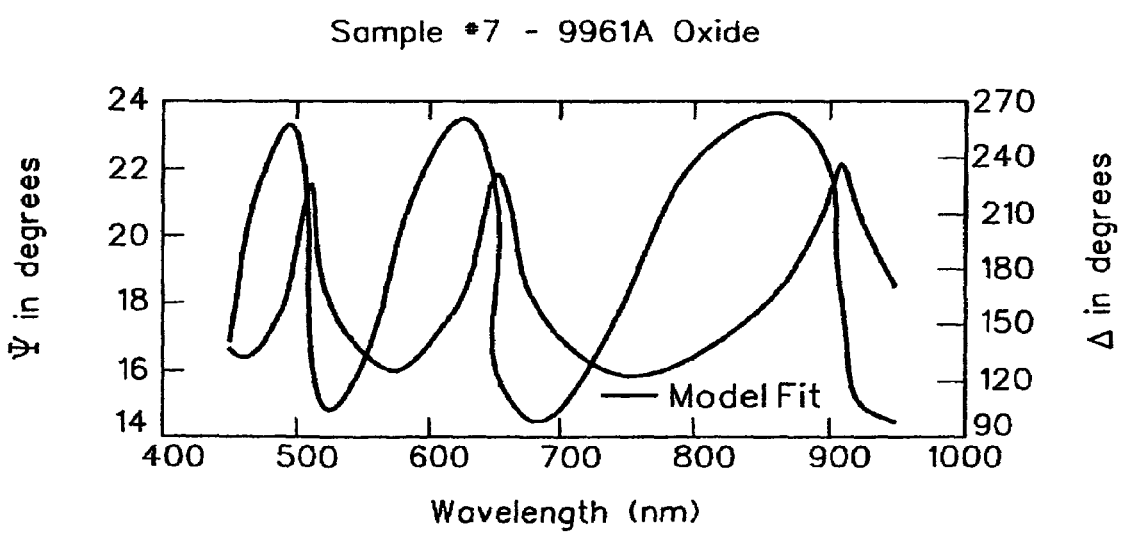

FIGS. 19 & 20 show PSI and DELTA values obtained for samples with thin (native), and thick, (9961 Angstrom), layers of Oxide thereupon. All results were obtained by fitting a mathematical model of the sample system and the spectroscopic ellipsometer system by regression onto experimental data.

Figure 21:
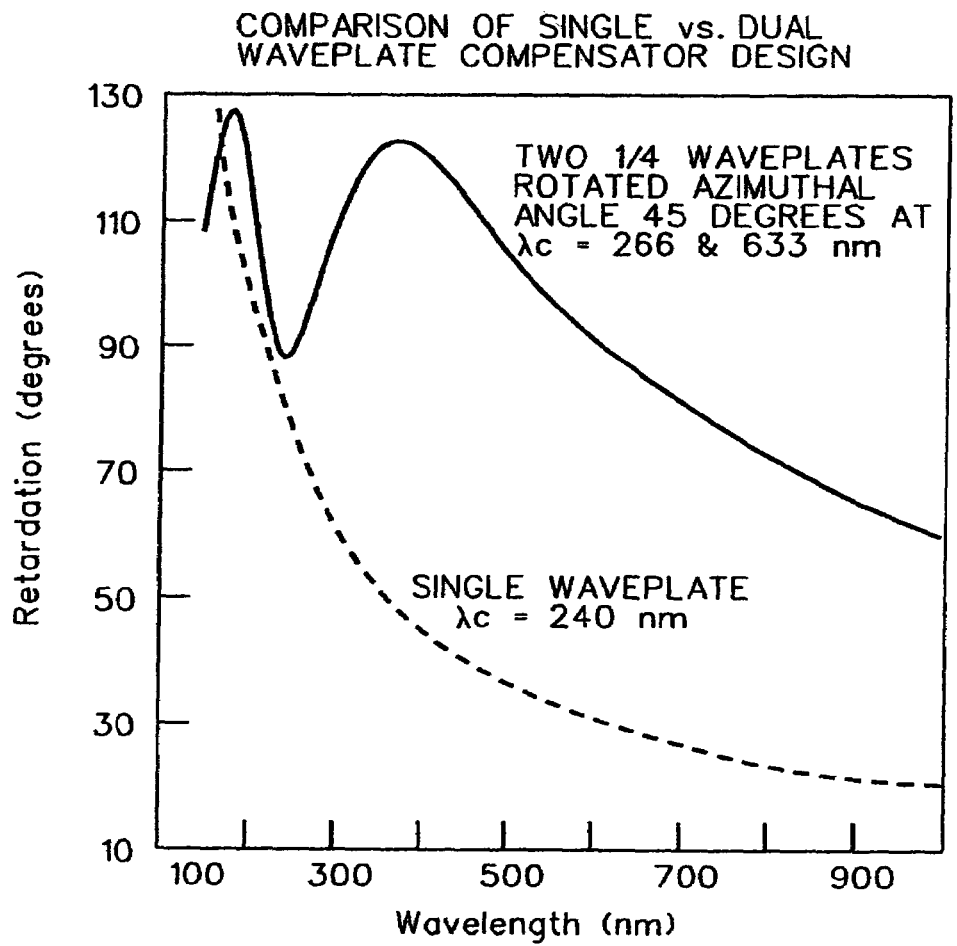
FIGS. 21-23 provide insight to the Psuedo-Achromatic characteristics achieved by a FIG. 10f Compensator design.
Figure 22:
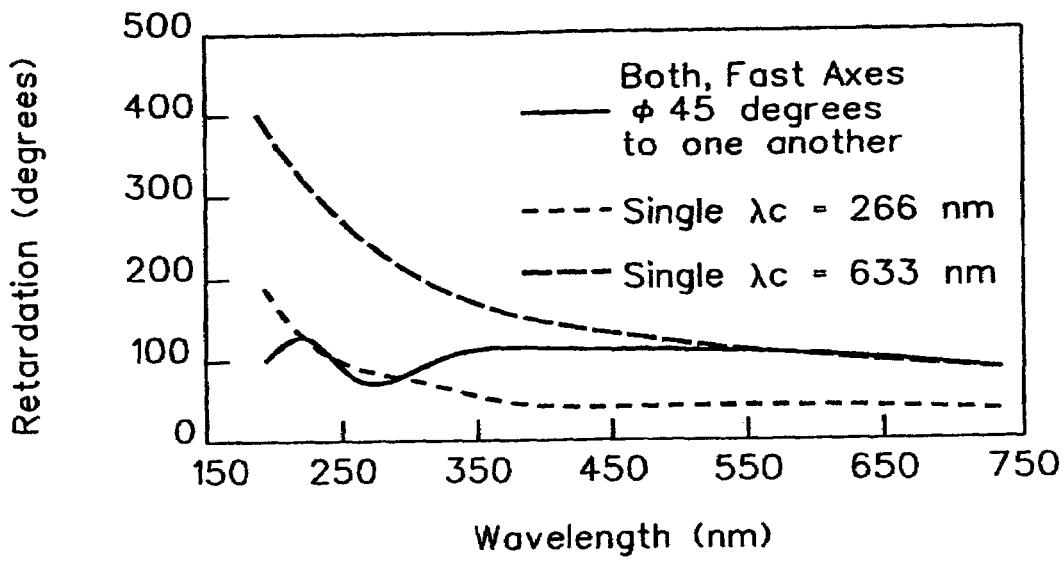
Figure 23:
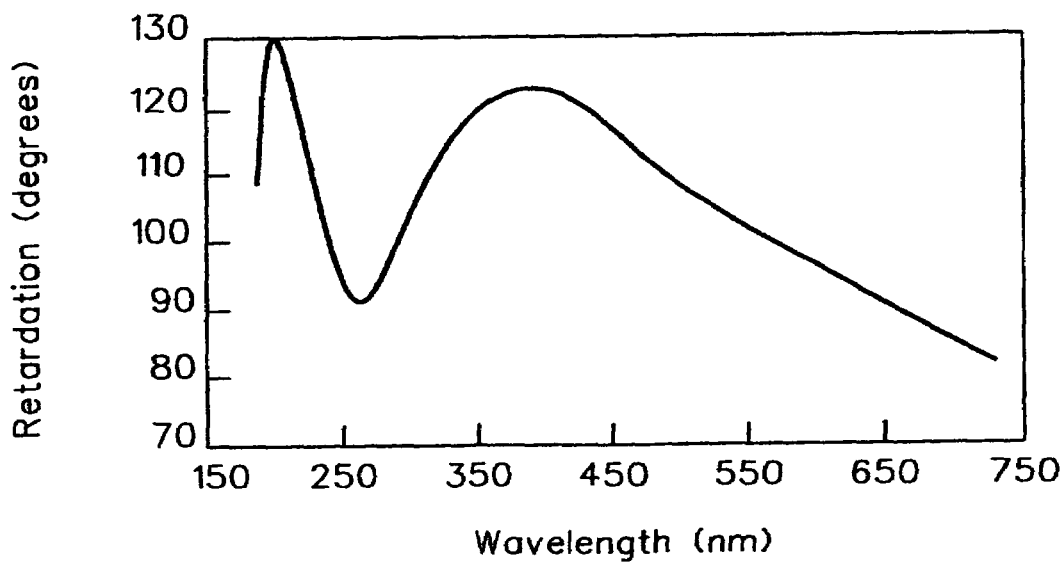

FIGS. 21-23 are also included herein to provide insight to the Psuedo-Achromatic characteristics achieved by the FIG. 10f Compensator design. FIG. 21 shows a plot of such a compensator retardation characteristic which depends as (1/wavelength), (dashed line), as well as a present invention compensator characteristic, (solid line). The important thing to note is that a selected range of wavelengths over which a retardation of between seventy-five (75) and one-hundred-thirty (130) degrees is developed, is much greater for the present invention compensator. A present invention spectroscopic rotatable compensator ellipsometer system can comprise at least one compensator(s) which produces a retardance of, preferably, between seventy-five (75) and one-hundred-thirty (130) degrees over a range of wavelengths defined by a selection from the group consisting of:
  a. between one-hundred-ninety (190) and seven-hundred-fifty (750) nanometers;
  b. between two-hundred-forty-five (245) and nine-hundred (900) nanometers;
  c. between three-hundred-eighty (380) and seventeen-hundred (1700) nanometers;
  d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, provides for the case wherein at least one of said at least one compensator(s) provides a retardation vs. wavelength characteristic retardation between thirty (30.0) and less than one-hundred-thirty-five (135) degrees over a range of wavelengths specified from MINW to MAXW by a selection from the group consisting of:
  a. MINW less than/equal to one-hundred-ninety (190) and MAXW greater than/equal to seventeen-hundred (1700);
  b. MINW less than/equal to two-hundred-twenty (220) and MAXW greater than/equal to one-thousand (1000) nanometers;
  c. within a range of wavelengths defined by a maximum wavelength (MAXW) and a minimum wavelength (MINW) range where (MAXW)/(MINW) is at least four- and one-half (4.5).

(NOTE, the specified vales and ranges can not be achieved by single plates with (1/wavelength) retardation characteristics).

More specifically, FIG. 22 shows calculated retardation vs. wavelength curves for two compensators which demonstrate (1/wavelength) retardation characteristics, (long and short dashed lines), and the retardation curve, (solid line), of a present invention assembly configuration as demonstrated in FIG. 10f which is arrived at by combining said two retarders with a 45 degree angle between the fast axes thereof. FIG. 23 shows a re-scaled plot of the solid line curve shown in FIG. 22.

It is to be understood that the effect of reflection of a spectroscopic beam by a electromagnetic beam chromatic shifting and directing means, which can comprise a silicon substrate with between 500 and 1500 Angstroms of silicon dioxide substantially uniformly present on a reflective surface thereof, is to de-emphasize intensity in visual wavelengths while simultaneously relatively emphasizing both IR and UV wavelength intensities. This allows increasing the intensity of a source of said spectroscopic beam without causing saturation of circuitry in a detector of said reflected beam.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An electromagnetic beam chromatic shifting and directing means for use in reflectively directing a spectroscopic beam of electromagnetic radiation while simultaneously de-emphasizing intensity in one range of wavelengths and emphasizing wavelength intensity outside said range, said electromagnetic beam chromatic shifting and directing means comprising at least:
  a substrate made of a first material, and
  a layer of a second material on a surface thereof;
such that in use a spectroscopic beam of electromagnetic radiation, which is characterized by a first intensity vs. wavelength spectrum, is caused to impinge, at an oblique angle of incidence, on the layer of said second material of said electromagnetic beam chromatic shifting and directing means so that it reflects with a second intensity vs. wavelength spectrum that is altered from that of said first intensity vs. wavelength spectrum.

2. An electromagnetic beam chromatic shifting and directing means as in claim 1 wherein the range of wavelengths wherein intensity is de-emphasized is the visible range of wavelengths, and wherein the wavelength intensities outside said range are in at least the UV range.

3. An electromagnetic beam chromatic shifting and directing means as in claim 2, wherein said electromagnetic beam chromatic shifting and directing means comprises silicon substrate made of silicon and wherein second material on said surface thereof is between 500 and 1500 Angstroms of silicon dioxide substantially uniformly present thereupon.

4. A method of providing a spectroscopic beam of electromagnetic radiation having wavelengths in at least UV and Visible wavelengths, comprising the steps of:
  a) providing a source of spectroscopic electromagnetic radiation which is characterized by a first intensity vs. wavelength spectrum;
  b) providing an electromagnetic beam chromatic shifting and directing means for use in reflectively directing a spectroscopic beam of electromagnetic radiation while simultaneously de-emphasizing intensity in one range of wavelengths and emphasizing wavelength intensity outside said range, said electromagnetic beam chromatic shifting and directing means comprising at least:
a substrate made of a first material, and
a layer of a second material on a surface thereof;

such that in use a spectroscopic beam of electromagnetic radiation, which is characterized by a first intensity vs. wavelength spectrum, is caused to impinge, at an oblique angle of incidence, on the layer of said second material of said electromagnetic beam chromatic shifting and directing means so that it reflects with a second intensity vs. wavelength spectrum that is altered from that of said first intensity vs. wavelength spectrum;

c) causing said source of spectroscopic electromagnetic radiation to provide a beam thereof and directing it to impinge upon said electromagnetic beam chromatic shifting and directing means at an oblique angle such that a reflected beam of electromagnetic radiation is produced, said reflected beam of electromagnetic radiation characterized by a second intensity vs. wavelength range having decreased intensity in visual range wavelengths, as compared to the intensity in said visible range wavelengths in the spectroscopic beam directly provided by said source of spectroscopic electromagnetic radiation.

5. A method as in claim 4 which further comprises increasing the intensity of the beam provided by said source of spectroscopic electromagnetic radiation, in all wavelength ranges.

6. A method as in claim 4 which further comprises causing said reflected beam to enter a detector.

7. An electromagnetic beam chromatic shifting and directing means as in claim 1, which further comprises a source of spectroscopic electromagnetic radiation that provides wavelengths in at least first and second ranges, and a detector situated such that in use said source provides a beam of electromagnetic radiation and directs it to impinge upon said electromagnetic beam chromatic shifting and directing means at an oblique angle of incidence, such that a reflected beam of electromagnetic radiation is produced and enters said detector.

8. An electromagnetic beam chromatic shifting and directing means as in claim 7, in which said first range of wavelengths is the visible range of wavelengths and said second range comprises at least UV wavelengths, and in which said electromagnetic beam chromatic shifting and directing means in combination with said source of spectroscopic electromagnetic radiation and said detector, comprise a selection from the group consisting of:
a reflectometer;
a spectrophotometer;
an ellipsometer; and
a polarimeter;
system.

9. An electromagnetic beam chromatic shifting and directing means as in claim 8, in which said electromagnetic beam chromatic shifting and directing means in which the substrate first material is silicon and the layer of a second material on said surface thereof is between 500 and 1500 Angstroms of silicon dioxide substantially uniformly present on said surface thereof.

10. A method as in claim 5 in which the step of providing an electromagnetic beam chromatic shifting and directing means for use in reflectively directing a spectroscopic beam of electromagnetic radiation involves providing a silicon substrate with between 500 and 1500 Angstroms of silicon dioxide substantially uniformly present on a reflective surface thereof.

11. A method as in claim 4, in which the electromagnetic beam chromatic shifting and directing means in combination with said source of spectroscopic electromagnetic radiation and said detector thereof, comprise a selection from the group consisting of:
a reflectometer;
a spectrophotometer;
an ellipsometer; and
a polarimeter;
system.

* * * * *